(12) United States Patent
Cheong et al.

(10) Patent No.: US 10,815,510 B2
(45) Date of Patent: Oct. 27, 2020

(54) **MICROORGANISM OF THE GENUS *ESCHERICHIA* PRODUCING L-TRYPTOPHAN AND METHOD FOR PRODUCING L-TRYPTOPHAN USING THE SAME**

(71) Applicant: CJ CHEILJEDANG CORPORATION, Seoul (KR)

(72) Inventors: Ki Yong Cheong, Gyeonggi-do (KR); Kyung Rim Kim, Seoul (KR); Seok Myung Lee, Seoul (KR); Kwang Ho Lee, Seoul (KR); Keun Cheol Lee, Gyeonggi-do (KR); Hyeong Pyo Hong, Gangwon-do (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 15/321,717

(22) PCT Filed: Jun. 23, 2015

(86) PCT No.: PCT/KR2015/006350
§ 371 (c)(1),
(2) Date: Dec. 22, 2016

(87) PCT Pub. No.: WO2015/199406
PCT Pub. Date: Dec. 30, 2015

(65) Prior Publication Data
US 2017/0137854 A1 May 18, 2017

(30) Foreign Application Priority Data

Jun. 23, 2014 (KR) .................. 10-2014-0076698

(51) Int. Cl.
C12P 13/22 (2006.01)
C12N 1/21 (2006.01)
C12N 9/88 (2006.01)
C12N 15/52 (2006.01)

(52) U.S. Cl.
CPC .............. *C12P 13/227* (2013.01); *C12N 9/88* (2013.01); *C12N 15/52* (2013.01); *C12P 13/22* (2013.01); *C12Y 401/02014* (2013.01); *C12Y 402/01012* (2013.01)

(58) Field of Classification Search
None
See application file for complete search history.

(56) References Cited

U.S. PATENT DOCUMENTS 4,371,614 A * 2/1983 Anderson ............. C12P 13/227
435/108
2004/0142435 A1 7/2004 Gunji et al.
2005/0191684 A1 * 9/2005 Zimenkov ............. C12P 13/04
435/6.14
2006/0115878 A1 6/2006 Hara et al.
2010/0028956 A1 2/2010 Ju et al.

FOREIGN PATENT DOCUMENTS

| CN | 101052707 A | 10/2007 |
|---|---|---|
| JP | 2007-523625 A | 8/2007 |
| JP | 2010-521959 A | 7/2010 |
| KR | 10-2007-0006799 A | 1/2007 |
| KR | 10-2009-0092373 A | 9/2009 |
| KR | 10-2013-0082121 A | 7/2013 |
| RU | 2288268 C2 | 11/2006 |
| WO | WO 2005-080583 A2 | 9/2005 |
| WO | WO 2008-116853 A1 | 10/2008 |

OTHER PUBLICATIONS

GenBank, Accession No. NC_000913, 2004, www.ncbi.nlm.nih.gov.*
Kivero et al., 2D [1H, 13C] NMR Study of Carbon Fluxes during Glucose Utilization by *Escherichia coli* MG1655, Appl. Biochem. Microbiol., 2008, 44, 151-57.*
Cohen, Gluconokinase and the oxidative path of glucose-6-phosphate utilization, J. Biol. Chem., 1951, 189, 617-28.*
Baez-Viveros et al., "Metabolic transcription analysis of engineered *Escherichia coli* strains that overproduce L-phenylalanine," Microbial Cell Factories 6(30): 2007, 20 pages.
NCBI Reference Sequence: WP_001069467.1, "MULTISPECIES: phosphogluconate dehydratase [Enterobacteriaceae]," Aug. 28, 2013, one page.
NCBI Reference Sequence: WP_000800512.1, "MULTISPECIES: ketohydroxyglutarate aldolase [Enterobacteriaceae]," Aug. 28, 2013, one page.
Bocharov et al., "2D [ 1 H, 13 C] NMR study of carbon fluxes during glucose utilization by *Escherichia coli* MG1655," Applied Biochemistry and Microbiology 44(2):168-175 (2008).
Genbank Accession No. NP_416365.1, dated Oct. 11, 2018, 3 pages.
Genbank Accession No. NP_416364.1, dated Oct. 11, 2018, 3 pages.

* cited by examiner

Primary Examiner — Robert B Mondesi
Assistant Examiner — Todd M Epstein
(74) Attorney, Agent, or Firm — Cooley LLP

(57) ABSTRACT

The present application relates to a microorganism of the genus *Escherichia* producing L-tryptophan and, more specifically, to a microorganism of the genus *Escherichia* with improved activity of producing L-tryptophan by weakening or inactivating the activity of endogenous 6-phosphogluconate dehydratase and 2-keto-3-deoxy-6-phosphogluconate aldolase.

Additionally, the present application relates to a method for producing L-tryptophan using the microorganism of the genus *Escherichia*.

10 Claims, No Drawings
Specification includes a Sequence Listing.

SEQUENCE LISTING

```
<160> NUMBER OF SEQ ID NOS: 47

<210> SEQ ID NO 1
<211> LENGTH: 603
<212> TYPE: PRT
<213> ORGANISM: Escherichia coli
<220> FEATURE:
<221> NAME/KEY: PEPTIDE
<222> LOCATION: (1)..(603)
<223> OTHER INFORMATION: edd

<400> SEQUENCE: 1

Met Asn Pro Gln Leu Leu Arg Val Thr Asn Arg Ile Ile Glu Arg Ser
1               5                   10                  15

Arg Glu Thr Arg Ser Ala Tyr Leu Ala Arg Ile Glu Gln Ala Lys Thr
            20                  25                  30

Ser Thr Val His Arg Ser Gln Leu Ala Cys Gly Asn Leu Ala His Gly
        35                  40                  45

Phe Ala Ala Cys Gln Pro Glu Asp Lys Ala Ser Leu Lys Ser Met Leu
    50                  55                  60

Arg Asn Asn Ile Ala Ile Ile Thr Ser Tyr Asn Asp Met Leu Ser Ala
65                  70                  75                  80

His Gln Pro Tyr Glu His Tyr Pro Glu Ile Ile Arg Lys Ala Leu His
                85                  90                  95

Glu Ala Asn Ala Val Gly Gln Val Ala Gly Gly Val Pro Ala Met Cys
            100                 105                 110

Asp Gly Val Thr Gln Gly Gln Asp Gly Met Glu Leu Ser Leu Leu Ser
        115                 120                 125

Arg Glu Val Ile Ala Met Ser Ala Ala Val Gly Leu Ser His Asn Met
    130                 135                 140

Phe Asp Gly Ala Leu Phe Leu Gly Val Cys Asp Lys Ile Val Pro Gly
145                 150                 155                 160

Leu Thr Met Ala Ala Leu Ser Phe Gly His Leu Pro Ala Val Phe Val
                165                 170                 175

Pro Ser Gly Pro Met Ala Ser Gly Leu Pro Asn Lys Glu Lys Val Arg
            180                 185                 190
```

-continued

```
Ile Arg Gln Leu Tyr Ala Glu Gly Lys Val Asp Arg Met Ala Leu Leu
            195                 200                 205
Glu Ser Glu Ala Ala Ser Tyr His Ala Pro Gly Thr Cys Thr Phe Tyr
        210                 215                 220
Gly Thr Ala Asn Thr Asn Gln Met Val Val Glu Phe Met Gly Met Gln
225                 230                 235                 240
Leu Pro Gly Ser Ser Phe Val His Pro Asp Ser Pro Leu Arg Asp Ala
                245                 250                 255
Leu Thr Ala Ala Ala Arg Gln Val Thr Arg Met Thr Gly Asn Gly
            260                 265                 270
Asn Glu Trp Met Pro Ile Gly Lys Met Ile Asp Glu Lys Val Val Val
        275                 280                 285
Asn Gly Ile Val Ala Leu Leu Ala Thr Gly Gly Ser Thr Asn His Thr
    290                 295                 300
Met His Leu Val Ala Met Ala Arg Ala Ala Gly Ile Gln Ile Asn Trp
305                 310                 315                 320
Asp Asp Phe Ser Asp Leu Ser Asp Val Val Pro Leu Met Ala Arg Leu
                325                 330                 335
Tyr Pro Asn Gly Pro Ala Asp Ile Asn His Phe Gln Ala Ala Gly Gly
            340                 345                 350
Val Pro Val Leu Val Arg Glu Leu Leu Lys Ala Gly Leu Leu His Glu
        355                 360                 365
Asp Val Asn Thr Val Ala Gly Phe Gly Leu Ser Arg Tyr Thr Leu Glu
    370                 375                 380
Pro Trp Leu Asn Asn Gly Glu Leu Asp Trp Arg Glu Gly Ala Glu Lys
385                 390                 395                 400
Ser Leu Asp Ser Asn Val Ile Ala Ser Phe Glu Gln Pro Phe Ser His
                405                 410                 415
His Gly Gly Thr Lys Val Leu Ser Gly Asn Leu Gly Arg Ala Val Met
            420                 425                 430
Lys Thr Ser Ala Val Pro Val Glu Asn Gln Val Ile Glu Ala Pro Ala
        435                 440                 445
Val Val Phe Glu Ser Gln His Asp Val Met Pro Ala Phe Glu Ala Gly
    450                 455                 460
Leu Leu Asp Arg Asp Cys Val Val Val Arg His Gln Gly Pro Lys
465                 470                 475                 480
Ala Asn Gly Met Pro Glu Leu His Lys Leu Met Pro Pro Leu Gly Val
                485                 490                 495
Leu Leu Asp Arg Cys Phe Lys Ile Ala Leu Val Thr Asp Gly Arg Leu
            500                 505                 510
Ser Gly Ala Ser Gly Lys Val Pro Ser Ala Ile His Val Thr Pro Glu
        515                 520                 525
Ala Tyr Asp Gly Gly Leu Leu Ala Lys Val Arg Asp Gly Asp Ile Ile
    530                 535                 540
Arg Val Asn Gly Gln Thr Gly Glu Leu Thr Leu Leu Val Asp Glu Ala
545                 550                 555                 560
Glu Leu Ala Ala Arg Glu Pro His Ile Pro Asp Leu Ser Ala Ser Arg
                565                 570                 575
Val Gly Thr Gly Arg Glu Leu Phe Ser Ala Leu Arg Glu Lys Leu Ser
            580                 585                 590
Gly Ala Glu Gln Gly Ala Thr Cys Ile Thr Phe
        595                 600
```

<210> SEQ ID NO 2
<211> LENGTH: 1812
<212> TYPE: DNA
<213> ORGANISM: Escherichia coli
<220> FEATURE:
<221> NAME/KEY: gene
<222> LOCATION: (1)..(1812)
<223> OTHER INFORMATION: edd

<400> SEQUENCE: 2

| | | | | | | |
|---|---|---|---|---|---|---|
| atgaatccac | aattgttacg | cgtaacaaat | cgaatcattg | aacgttcgcg | cgagactcgc | 60 |
| tctgcttatc | tcgcccggat | agaacaagcg | aaaacttcga | ccgttcatcg | ttcgcagttg | 120 |
| gcatgcggta | acctggcaca | cggtttcgct | gcctgccagc | cagaagacaa | agcctctttg | 180 |
| aaaagcatgt | tgcgtaacaa | tatcgccatc | atcacctcct | ataacgacat | gctctccgcg | 240 |
| caccagcctt | atgaacacta | tccagaaatc | attcgtaaag | ccctgcatga | agcgaatgcg | 300 |
| gttggtcagg | ttgcgggcgg | tgttccggcg | atgtgtgatg | gtgtcaccca | ggggcaggat | 360 |
| ggaatggaat | gtcgctgct | aagccgcgaa | gtgatagcga | tgtctgcggc | ggtggggctg | 420 |
| tcccataaca | tgtttgatgg | tgctctgttc | ctcggtgtgt | gcgacaagat | tgtcccgggt | 480 |
| ctgacgatgg | cagccctgtc | gtttggtcat | ttgcctgcgg | tgtttgtgcc | gtctggaccg | 540 |
| atggcaagcg | gtttgccaaa | taagaaaaa | gtgcgtattc | gccagcttta | tgccgaaggt | 600 |
| aaagtggacc | gcatggcctt | actggagtca | gaagccgcgt | cttaccatgc | gccgggaaca | 660 |
| tgtactttct | acggtactgc | caacaccaac | cagatggtgg | tggagtttat | ggggatgcag | 720 |
| ttgccaggct | cttcttttgt | tcatccggat | tctccgctgc | gcgatgcttt | gaccgccgca | 780 |
| gctgcgcgtc | aggttacacg | catgaccggt | aatggtaatg | aatggatgcc | gatcggtaag | 840 |
| atgatcgatg | agaaagtggt | ggtgaacggt | atcgttgcac | tgctggcgac | cggtggttcc | 900 |
| actaaccaca | ccatgcacct | ggtggcgatg | gcgcgcgcgg | ccggtattca | gattaactgg | 960 |
| gatgacttct | ctgacctttc | tgatgttgta | ccgctgatgg | cacgtctcta | cccgaacggt | 1020 |
| ccggccgata | ttaaccactt | ccaggcggca | ggtggcgtac | cggttctggt | gcgtgaactg | 1080 |
| ctcaaagcag | gcctgctgca | tgaagatgtc | aatacggtgg | caggttttgg | tctgtctcgt | 1140 |
| tatacccttg | aacatggct | gaataatggt | gaactggact | ggcgggaagg | ggcggaaaaa | 1200 |
| tcactcgaca | gcaatgtgat | cgcttccttc | gaacaacctt | tctctcatca | tggtgggaca | 1260 |
| aaagtgttaa | gcggtaacct | gggccgtgcg | gttatgaaaa | cctctgccgt | gccggttgag | 1320 |
| aaccaggtga | ttgaagcgcc | agcggttgtt | tttgaaagcc | agcatgacgt | tatgccggcc | 1380 |
| tttgaagcgg | gtttgctgga | ccgcgattgt | gtcgttgttg | tccgtcatca | ggggccaaaa | 1440 |
| gcgaacggaa | tgccagaatt | acataaactc | atgccgccac | ttggtgtatt | attggaccgg | 1500 |
| tgtttcaaaa | ttgcgttagt | taccgatgga | cgactctccg | gcgcttcagg | taaagtgccg | 1560 |
| tcagctatcc | acgtaacacc | agaagcctac | gatggcgggc | tgctggcaaa | agtgcgcgac | 1620 |
| ggggacatca | ttcgtgtgaa | tggacagaca | ggcgaactga | cgctgctggt | agacgaagcg | 1680 |
| gaactggctg | ctcgcgaacc | gcacattcct | gacctgagcg | cgtcacgcgt | gggaacagga | 1740 |
| cgtgaattat | tcagcgcctt | gcgtgaaaaa | ctgtccggtg | ccgaacaggg | cgcaacctgt | 1800 |
| atcacttttt | aa | | | | | 1812 |

<210> SEQ ID NO 3
<211> LENGTH: 213
<212> TYPE: PRT
<213> ORGANISM: Escherichia coli

```
<220> FEATURE:
<221> NAME/KEY: PEPTIDE
<222> LOCATION: (1)..(213)
<223> OTHER INFORMATION: eda

<400> SEQUENCE: 3
```

Met Lys Asn Trp Lys Thr Ser Ala Glu Ser Ile Leu Thr Thr Gly Pro
1               5                   10                  15

Val Val Pro Val Ile Val Lys Lys Leu Glu His Ala Val Pro Met
            20                  25                  30

Ala Lys Ala Leu Val Ala Gly Gly Val Arg Val Leu Glu Val Thr Leu
        35                  40                  45

Arg Thr Glu Cys Ala Val Asp Ala Ile Arg Ala Ile Ala Lys Glu Val
    50                  55                  60

Pro Glu Ala Ile Val Gly Ala Gly Thr Val Leu Asn Pro Gln Gln Leu
65                  70                  75                  80

Ala Glu Val Thr Glu Ala Gly Ala Gln Phe Ala Ile Ser Pro Gly Leu
            85                  90                  95

Thr Glu Pro Leu Leu Lys Ala Ala Thr Glu Gly Thr Ile Pro Leu Ile
            100                 105                 110

Pro Gly Ile Ser Thr Val Ser Glu Leu Met Leu Gly Met Asp Tyr Gly
        115                 120                 125

Leu Lys Glu Phe Lys Phe Phe Pro Ala Glu Ala Asn Gly Gly Val Lys
130                 135                 140

Ala Leu Gln Ala Ile Ala Gly Pro Phe Ser Gln Val Arg Phe Cys Pro
145                 150                 155                 160

Thr Gly Gly Ile Ser Pro Ala Asn Tyr Arg Asp Tyr Leu Ala Leu Lys
                165                 170                 175

Ser Val Leu Cys Ile Gly Gly Ser Trp Leu Val Pro Asp Ala Leu
            180                 185                 190

Glu Ala Gly Asp Tyr Asp Arg Ile Thr Lys Leu Ala Arg Glu Ala Val
            195                 200                 205

Glu Gly Ala Lys Leu
        210

```
<210> SEQ ID NO 4
<211> LENGTH: 642
<212> TYPE: DNA
<213> ORGANISM: Escherichia coli
<220> FEATURE:
<221> NAME/KEY: gene
<222> LOCATION: (1)..(642)
<223> OTHER INFORMATION: eda

<400> SEQUENCE: 4
atgaaaaact ggaaaacaag tgcagaatca atcctgacca ccggcccggt tgtaccggtt     60
atcgtggtaa aaaaactgga acacgcggtg ccgatggcaa aagcgttggt tgctggtggg    120
gtgcgcgttc tggaagtgac tctgcgtacc gagtgtgcag ttgacgctat ccgtgctatc    180
gccaaagaag tgcctgaagc gattgtgggt gccggtacgg tgctgaatcc acagcagctg    240
gcagaagtca ctgaagcggg tgcacagttc gcaattagcc cgggtctgac cgagccgctg    300
ctgaaagctg ctaccgaagg gactattcct ctgattccgg ggatcagcac tgtttccgaa    360
ctgatgctgg gtatggacta cggttttgaa gagttcaaat tcttcccggc tgaagctaac    420
ggcggcgtga aagccctgca ggcgatcgcg ggtccgttct cccaggtccg tttctgcccg    480
acgggtggta tttctccggc taactaccgt gactacctgg cgctgaaaag cgtgctgtgc    540
```

```
atcggtggtt cctggctggt tccggcagat gcgctggaag cgggcgatta cgaccgcatt    600
actaagctgg cgcgtgaagc tgtagaaggc gctaagctgt aa                       642
```

<210> SEQ ID NO 5
<211> LENGTH: 386
<212> TYPE: PRT
<213> ORGANISM: Escherichia coli
<220> FEATURE:
<221> NAME/KEY: PEPTIDE
<222> LOCATION: (1)..(386)
<223> OTHER INFORMATION: pheA

<400> SEQUENCE: 5

```
Met Thr Ser Glu Asn Pro Leu Leu Ala Leu Arg Glu Lys Ile Ser Ala
 1               5                  10                  15

Leu Asp Glu Lys Leu Leu Ala Leu Leu Ala Glu Arg Arg Glu Leu Ala
                20                  25                  30

Val Glu Val Gly Lys Ala Lys Leu Leu Ser His Arg Pro Val Arg Asp
             35                  40                  45

Ile Asp Arg Glu Arg Asp Leu Leu Glu Arg Leu Ile Thr Leu Gly Lys
 50                  55                  60

Ala His His Leu Asp Ala His Tyr Ile Thr Arg Leu Phe Gln Leu Ile
 65                  70                  75                  80

Ile Glu Asp Ser Val Leu Thr Gln Gln Ala Leu Leu Gln Gln His Leu
                 85                  90                  95

Asn Lys Ile Asn Pro His Ser Ala Arg Ile Ala Phe Leu Gly Pro Lys
            100                 105                 110

Gly Ser Tyr Ser His Leu Ala Ala Arg Gln Tyr Ala Ala Arg His Phe
        115                 120                 125

Glu Gln Phe Ile Glu Ser Gly Cys Ala Lys Phe Ala Asp Ile Phe Asn
    130                 135                 140

Gln Val Glu Thr Gly Gln Ala Asp Tyr Ala Val Val Pro Ile Glu Asn
145                 150                 155                 160

Thr Ser Ser Gly Ala Ile Asn Asp Val Tyr Asp Leu Leu Gln His Thr
                165                 170                 175

Ser Leu Ser Ile Val Gly Glu Met Thr Leu Thr Ile Asp His Cys Leu
            180                 185                 190

Leu Val Ser Gly Thr Thr Asp Leu Ser Thr Ile Asn Thr Val Tyr Ser
        195                 200                 205

His Pro Gln Pro Phe Gln Gln Cys Ser Lys Phe Leu Asn Arg Tyr Pro
    210                 215                 220

His Trp Lys Ile Glu Tyr Thr Glu Ser Thr Ser Ala Ala Met Glu Lys
225                 230                 235                 240

Val Ala Gln Ala Lys Ser Pro His Val Ala Ala Leu Gly Ser Glu Ala
                245                 250                 255

Gly Gly Thr Leu Tyr Gly Leu Gln Val Leu Glu Arg Ile Glu Ala Asn
            260                 265                 270

Gln Arg Gln Asn Phe Thr Arg Phe Val Val Leu Ala Arg Lys Ala Ile
        275                 280                 285

Asn Val Ser Asp Gln Val Pro Ala Lys Thr Thr Leu Leu Met Ala Thr
    290                 295                 300

Gly Gln Gln Ala Gly Ala Leu Val Glu Ala Leu Leu Val Leu Arg Asn
305                 310                 315                 320

His Asn Leu Ile Met Thr Arg Leu Glu Ser Arg Pro Ile His Gly Asn
                325                 330                 335
```

Pro Trp Glu Glu Met Phe Tyr Leu Asp Ile Gln Ala Asn Leu Glu Ser
         340                 345                 350

Ala Glu Met Gln Lys Ala Leu Lys Glu Leu Gly Glu Ile Thr Arg Ser
         355                 360                 365

Met Lys Val Leu Gly Cys Tyr Pro Ser Glu Asn Val Val Pro Val Asp
         370                 375                 380

Pro Thr
385

<210> SEQ ID NO 6
<211> LENGTH: 1161
<212> TYPE: DNA
<213> ORGANISM: Escherichia coli
<220> FEATURE:
<221> NAME/KEY: gene
<222> LOCATION: (1)..(1161)
<223> OTHER INFORMATION: pheA

<400> SEQUENCE: 6

```
atgacatcgg aaaacccgtt actggcgctg cgagagaaaa tcagcgcgct ggatgaaaaa      60
ttattagcgt tactggcaga acggcgcgaa ctggccgtcg aggtgggaaa agccaaactg     120
ctctcgcatc gcccggtacg tgatattgat cgtgaacgcg atttgctgga agattaatt     180 acgctcggta aagcgcacca tctggacgcc attacatta ctcgcctgtt ccagctcatc     240
attgaagatt ccgtattaac tcagcaggct ttgctccaac aacatctcaa taaaattaat     300
ccgcactcag cacgcatcgc tttctcggc cccaaaggtt cttattccca tcttgcggcg     360
cgccagtatg ctgcccgtca ctttgagcaa ttcattgaaa gtggctgcgc caatttgcc     420 gatattttta atcaggtgga aaccggccag ccgactatg ccgtcgtacc gattgaaaat     480
accagctccg gtgccataaa cgacgtttac gatctgctgc aacataccag cttgtcgatt     540
gttggcgaga tgacgttaac tatcgaccat tgtttgttgg tctccggcac tactgattta     600
tccaccatca atacggtcta cagccatccg cagccattcc agcaatgcag caaattcctt     660
aatcgttatc cgcactggaa gattgaatat accgaaagta cgtctgcggc aatggaaaag     720
gttgcacagg caaatcacc gcatgttgct gcgttgggaa gcgaagctgg cggcactttg     780
tacggtttgc aggtactgga gcgtattgaa gcaaatcagc gacaaaactt cacccgattt     840
gtggtgttgg cgcgtaaagc cattaacgtg tctgatcagg ttccggcgaa accacgttg     900 ttaatggcga ccgggcaaca agccggtgcg ctggttgaag cgttgctggt actgcgcaac     960
cacaatctga ttatgacccg tctggaatca cgcccgattc acggtaatcc atgggaagag    1020
atgttctatc tggatattca ggccaatctt gaatcagcgg aaatgcaaaa agcattgaaa    1080
gagttagggg aaatcacccg ttcaatgaag gtattgggct gttacccaag tgagaacgta    1140
gtgcctgttg atccaaacctg a                                                     1161
```

<210> SEQ ID NO 7
<211> LENGTH: 108
<212> TYPE: PRT
<213> ORGANISM: Escherichia coli
<220> FEATURE:
<221> NAME/KEY: PEPTIDE
<222> LOCATION: (1)..(108)
<223> OTHER INFORMATION: trpR

```
<400> SEQUENCE: 7

Met Ala Gln Gln Ser Pro Tyr Ser Ala Ala Met Ala Glu Gln Arg His
1               5                   10                  15

Gln Glu Trp Leu Arg Phe Val Asp Leu Leu Lys Asn Ala Tyr Gln Asn
            20                  25                  30

Asp Leu His Leu Pro Leu Leu Asn Leu Met Leu Thr Pro Asp Glu Arg
        35                  40                  45

Glu Ala Leu Gly Thr Arg Val Arg Ile Val Glu Glu Leu Leu Arg Gly
    50                  55                  60

Glu Met Ser Gln Arg Glu Leu Lys Asn Glu Leu Gly Ala Gly Ile Ala
65                  70                  75                  80

Thr Ile Thr Arg Gly Ser Asn Ser Leu Lys Ala Ala Pro Val Glu Leu
                85                  90                  95

Arg Gln Trp Leu Glu Glu Val Leu Leu Lys Ser Asp
            100                 105

<210> SEQ ID NO 8
<211> LENGTH: 327
<212> TYPE: DNA
<213> ORGANISM: Escherichia coli
<220> FEATURE:
<221> NAME/KEY: gene
<222> LOCATION: (1)..(327)
<223> OTHER INFORMATION: trpR

<400> SEQUENCE: 8
atggcccaac aatcacccta ttcagcagcg atggcagaac agcgtcacca ggagtggtta      60
cgttttgtcg acctgcttaa gaatgcctac caaaacgatc tccatttacc gttgttaaac    120
ctgatgctga cgccagatga gcgcgaagcg ttggggactc gcgtgcgtat tgtcgaagag    180
ctgttgcgcg gcgaaatgag ccagcgtgag ttaaaaaatg aactcggcgc aggcatcgcg    240
acgattacgc gtggatctaa cagcctgaaa gccgcgcccg tcgagctgcg ccagtggctg    300
gaagaggtgt tgctgaaaag cgattga                                        327

<210> SEQ ID NO 9
<211> LENGTH: 414
<212> TYPE: PRT
<213> ORGANISM: Escherichia coli
<220> FEATURE:
<221> NAME/KEY: PEPTIDE
<222> LOCATION: (1)..(414)
<223> OTHER INFORMATION: mtr

<400> SEQUENCE: 9

Met Ala Thr Leu Thr Thr Thr Gln Thr Ser Pro Ser Leu Leu Gly Gly
1               5                   10                  15

Val Val Ile Ile Gly Gly Thr Ile Ile Gly Ala Gly Met Phe Ser Leu
            20                  25                  30

Pro Val Val Met Ser Gly Ala Trp Phe Phe Trp Ser Met Ala Ala Leu
        35                  40                  45

Ile Phe Thr Trp Phe Cys Met Leu His Ser Gly Leu Met Ile Leu Glu
    50                  55                  60

Ala Asn Leu Asn Tyr Arg Ile Gly Ser Ser Phe Asp Thr Ile Thr Lys
65                  70                  75                  80

Asp Leu Leu Gly Lys Gly Trp Asn Val Val Asn Gly Ile Ser Ile Ala
                85                  90                  95

Phe Val Leu Tyr Ile Leu Thr Tyr Ala Tyr Ile Ser Ala Ser Gly Ser
            100                 105                 110
```

Ile Leu His His Thr Phe Ala Glu Met Ser Leu Asn Val Pro Ala Arg
            115                 120                 125

Ala Ala Gly Phe Gly Phe Ala Leu Leu Val Ala Phe Val Val Trp Leu
        130                 135                 140

Ser Thr Lys Ala Val Ser Arg Met Thr Ala Ile Val Leu Gly Ala Lys
145                 150                 155                 160

Val Ile Thr Phe Phe Leu Thr Phe Gly Ser Leu Leu Gly His Val Gln
                165                 170                 175

Pro Ala Thr Leu Phe Asn Val Ala Glu Ser Asn Ala Ser Tyr Ala Pro
            180                 185                 190

Tyr Leu Leu Met Thr Leu Pro Phe Cys Leu Ala Ser Phe Gly Tyr His
        195                 200                 205

Gly Asn Val Pro Ser Leu Met Lys Tyr Tyr Gly Lys Asp Pro Lys Thr
210                 215                 220

Ile Val Lys Cys Leu Val Tyr Gly Thr Leu Met Ala Leu Ala Leu Tyr
225                 230                 235                 240

Thr Ile Trp Leu Leu Ala Thr Met Gly Asn Ile Pro Arg Pro Glu Phe
                245                 250                 255

Ile Gly Ile Ala Glu Lys Gly Gly Asn Ile Asp Val Leu Val Gln Ala
            260                 265                 270

Leu Ser Gly Val Leu Asn Ser Arg Ser Leu Asp Leu Leu Leu Val Val
        275                 280                 285

Phe Ser Asn Phe Ala Val Ala Ser Ser Phe Leu Gly Val Thr Leu Gly
        290                 295                 300

Leu Phe Asp Tyr Leu Ala Asp Leu Phe Gly Phe Asp Asp Ser Ala Val
305                 310                 315                 320

Gly Arg Leu Lys Thr Ala Leu Leu Thr Phe Ala Pro Pro Val Val Gly
                325                 330                 335

Gly Leu Leu Phe Pro Asn Gly Phe Leu Tyr Ala Ile Gly Tyr Ala Gly
            340                 345                 350

Leu Ala Ala Thr Ile Trp Ala Ala Ile Val Pro Ala Leu Leu Ala Arg
        355                 360                 365

Ala Ser Arg Lys Arg Phe Gly Ser Pro Lys Phe Arg Val Trp Gly Gly
        370                 375                 380

Lys Pro Met Ile Ala Leu Ile Leu Val Phe Gly Val Gly Asn Ala Leu
385                 390                 395                 400

Val His Ile Leu Ser Ser Phe Asn Leu Leu Pro Val Tyr Gln
                405                 410

<210> SEQ ID NO 10
<211> LENGTH: 1245
<212> TYPE: DNA
<213> ORGANISM: Escherichia coli
<220> FEATURE:
<221> NAME/KEY: gene
<222> LOCATION: (1)..(1245)
<223> OTHER INFORMATION: mtr

<400> SEQUENCE: 10
atggcaacac taaccaccac ccaaacgtca ccgtcgctgc ttggcggcgt ggtgattatc        60
ggcggcacca ttattggcgc agggatgttt tctctgccag tggtcatgtc cggggcgtgg       120
tttttctggt caatggcggc gctgatcttt acctggttct gtatgctgca ttccggcttg       180
atgattctgg aagctaacct gaattacaga atcggttcga gttttgacac catcaccaaa       240
gatttgctgg gcaaaggctg gaacgtggtc aacggcattt ccattgcctt gtgtgctcta       300

-continued

```
atcctgacct atgcctatat ttctgccagt ggttcgattc tgcatcacac cttcgcagag    360
atgtcactaa acgtcccggc acgggcggcg ggttttggtt ttgcattgct ggtagcgttt    420
gtggtgtggt tgagcactaa agccgtcagt cgcatgacag cgattgtgct ggggggcgaaa    480 gtcattacct tcttcctcac ctttggtagc ctgctggggc atgtgcagcc tgcgacattg    540
ttcaacgtcg ccgaaagcaa tgcgtcttat gcaccgtatc tgttgatgac cctgccgttc    600
tgtctggcat cgtttggtta tcacggtaac gtgccaagcc tgatgaagta ttacggcaaa    660
gatccgaaaa ccatcgtgaa atgtctggtg tacggtacgc tgatggcgct ggcgctgtat    720
accatctggt tgctggcgac gatgggtaac atcccgcgtc cggagtttat cggtattgca    780
gagaagggcg gtaatattga tgtgctggta caggcgttaa gcggcgtact gaacagccgt    840
agtctggatc tgctgctggt cgtgttctca aactttgcgg tagcgagttc gttcctcggc    900
gtaacgctgg gtttgtttga ctatctggca gatctgtttg gtttcgacga ctcggctgtg    960
ggccgcttga aaacggcatt gctgaccttt gccccgccag ttgtgggggg gctgttgttc    1020
ccgaacggat tcctgtacgc cattggttat gctggtttag cggctaccat ctgggcggca    1080
attgttccgg cgctgttagc ccgtgcatcg cgtaaacgct ttggcagccc gaaattccgc    1140
gtctggggtg gcaagccgat gattgcgctg attctggtgt ttggcgtcgg caacgcactg    1200
gtgcatattt tatcgagctt taatttactg ccggtgtatc agtaa                   1245
```

<210> SEQ ID NO 11
<211> LENGTH: 471
<212> TYPE: PRT
<213> ORGANISM: Escherichia coli
<220> FEATURE:
<221> NAME/KEY: PEPTIDE
<222> LOCATION: (1)..(471)
<223> OTHER INFORMATION: tnaA

<400> SEQUENCE: 11

```
Met Glu Asn Phe Lys His Leu Pro Glu Pro Phe Arg Ile Arg Val Ile
1               5                   10                  15

Glu Pro Val Lys Arg Thr Thr Arg Ala Tyr Arg Glu Glu Ala Ile Ile
            20                  25                  30

Lys Ser Gly Met Asn Pro Phe Leu Leu Asp Ser Glu Asp Val Phe Ile
        35                  40                  45

Asp Leu Leu Thr Asp Ser Gly Thr Gly Ala Val Thr Gln Ser Met Gln
    50                  55                  60

Ala Ala Met Met Arg Gly Asp Glu Ala Tyr Ser Gly Ser Arg Ser Tyr
65                  70                  75                  80

Tyr Ala Leu Ala Glu Ser Val Lys Asn Ile Phe Gly Tyr Gln Tyr Thr
                85                  90                  95

Ile Pro Thr His Gln Gly Arg Gly Ala Glu Gln Ile Tyr Ile Pro Val
            100                 105                 110

Leu Ile Lys Lys Arg Glu Gln Glu Lys Gly Leu Asp Arg Ser Lys Met
        115                 120                 125

Val Ala Phe Ser Asn Tyr Phe Phe Asp Thr Thr Gln Gly His Ser Gln
    130                 135                 140

Ile Asn Gly Cys Thr Val Arg Asn Val Tyr Ile Lys Glu Ala Phe Asp
145                 150                 155                 160

Thr Gly Val Arg Tyr Asp Phe Lys Gly Asn Phe Asp Leu Glu Gly Leu
                165                 170                 175

Glu Arg Gly Ile Glu Glu Val Gly Pro Asn Asn Val Pro Tyr Ile Val
            180                 185                 190
```

```
Ala Thr Ile Thr Ser Asn Ser Ala Gly Gly Gln Pro Val Ser Leu Ala
            195                 200                 205

Asn Leu Lys Ala Met Tyr Ser Ile Ala Lys Lys Tyr Asp Ile Pro Val
210                 215                 220

Val Met Asp Ser Ala Arg Phe Ala Glu Asn Ala Tyr Phe Ile Lys Gln
225                 230                 235                 240

Arg Glu Ala Glu Tyr Lys Asp Trp Thr Ile Glu Gln Ile Thr Arg Glu
            245                 250                 255

Thr Tyr Lys Tyr Ala Asp Met Leu Ala Met Ser Ala Lys Lys Asp Ala
                260                 265                 270

Met Val Pro Met Gly Gly Leu Leu Cys Met Lys Asp Asp Ser Phe Phe
            275                 280                 285

Asp Val Tyr Thr Glu Cys Arg Thr Leu Cys Val Val Gln Glu Gly Phe
290                 295                 300

Pro Thr Tyr Gly Gly Leu Glu Gly Gly Ala Met Glu Arg Leu Ala Val
305                 310                 315                 320

Gly Leu Tyr Asp Gly Met Asn Leu Asp Trp Leu Ala Tyr Arg Ile Ala
            325                 330                 335

Gln Val Gln Tyr Leu Val Asp Gly Leu Glu Glu Ile Gly Val Val Cys
                340                 345                 350

Gln Gln Ala Gly Gly His Ala Ala Phe Val Asp Ala Gly Lys Leu Leu
            355                 360                 365

Pro His Ile Pro Ala Asp Gln Phe Pro Ala Gln Ala Leu Ala Cys Glu
            370                 375                 380

Leu Tyr Lys Val Ala Gly Ile Arg Ala Val Glu Ile Gly Ser Phe Leu
385                 390                 395                 400

Leu Gly Arg Asp Pro Lys Thr Gly Lys Gln Leu Pro Cys Pro Ala Glu
                405                 410                 415

Leu Leu Arg Leu Thr Ile Pro Arg Ala Thr Tyr Thr Gln Thr His Met
            420                 425                 430

Asp Phe Ile Ile Glu Ala Phe Lys His Val Lys Glu Asn Ala Ala Asn
            435                 440                 445

Ile Lys Gly Leu Thr Phe Thr Tyr Glu Pro Lys Val Leu Arg His Phe
450                 455                 460

Thr Ala Lys Leu Lys Glu Val
465                 470
```

<210> SEQ ID NO 12
<211> LENGTH: 1416
<212> TYPE: DNA
<213> ORGANISM: Escherichia coli
<220> FEATURE:
<221> NAME/KEY: gene
<222> LOCATION: (1)..(1416)
<223> OTHER INFORMATION: tnaA

<400> SEQUENCE: 12

```
atggaaaact ttaaacatct ccctgaaccg ttccgcattc gtgttattga gccagtaaaa     60
cgtaccactc gcgcttatcg tgaagaggca attattaaat ccggtatgaa cccgttcctg    120
ctggatagcg aagatgtttt tatcgattta ctgaccgaca cgggcaccgg ggcggtgacg    180
cagagcatgc aggctgcgat gatgcgcggc gacgaagcct acagcggcag tcgtagctac    240
tatgcgttag ccgagtcagt gaaaaatatc tttggttatc aatacaccat tccgactcac    300
cagggccgtg gcgcagagca atctatatt ccggtactga ttaaaaaacg cgagcaggaa    360
aaaggcctgg atcgcagcaa aatggtggcg ttctctaact atttctttga taccacgcag    420
```

```
ggccatagcc agatcaacgg ctgtaccgtg cgtaacgtct atatcaaaga agccttcgat    480
acgggcgtgc gttacgactt taaaggcaac tttgaccttg agggattaga acgcggtatt    540
gaagaagttg gtccgaataa cgtgccgtat atcgttgcaa ccatcaccag taactctgca    600
ggtggtcagc cggtttcact ggcaaactta aaagcgatgt acagcatcgc gaagaaatac    660
gatattccgg tggtaatgga ctccgcgcgc tttgctgaaa acgcctattt catcaagcag    720
cgtgaagcag aatacaaaga ctggaccatc gagcagatca cccgcgaaac ctacaaatat    780
gccgatatgc tggcgatgtc cgccaagaaa gatgcgatgg tgccgatggg cggcctgctg    840
tgcatgaaag acgacagctt ctttgatgtg tacaccgagt gcagaaccct ttgcgtggtg    900
caggaaggct cccgacata tggcggcctg aaggcggcg cgatggagcg tctggcggta      960
ggtctgtatg acggcatgaa tctcgactgg ctggcttatc gtatcgcgca ggtacagtat    1020
ctggtcgatg gtctggaaga gattggcgtt gtctgccagc aggcgggcgg tcacgcggca    1080
ttcgttgatg ccggtaaact gttgccgcat atcccggcag accagttccc ggcacaggcg    1140
ctggcctgcg agctgtataa agtcgccggt atccgtgcgg tagaaattgg ctctttcctg    1200
ttaggccgcg atccgaaaac cggtaaacaa ctgccatgcc cggctgaact gctgcgttta    1260
accattccgc gcgcaacata tactcaaaca catatggact tcattattga agcctttaaa    1320
catgtgaaag agaacgcggc gaatattaaa ggattaacct ttacgtacga accgaaagta    1380
ttgcgtcact tcaccgcaaa acttaaagaa gtttaa                              1416
```

<210> SEQ ID NO 13
<211> LENGTH: 415
<212> TYPE: PRT
<213> ORGANISM: Escherichia coli
<220> FEATURE:
<221> NAME/KEY: PEPTIDE
<222> LOCATION: (1)..(415)
<223> OTHER INFORMATION: tnaB

<400> SEQUENCE: 13

```
Met Thr Asp Gln Ala Glu Lys Lys His Ser Ala Phe Trp Gly Val Met
1               5                   10                  15

Val Ile Ala Gly Thr Val Ile Gly Gly Met Phe Ala Leu Pro Val
            20                  25                  30

Asp Leu Ala Gly Ala Trp Phe Phe Trp Gly Ala Phe Ile Leu Ile Ile
        35                  40                  45

Ala Trp Phe Ser Met Leu His Ser Gly Leu Leu Leu Glu Ala Asn
    50                  55                  60

Leu Asn Tyr Pro Val Gly Ser Ser Phe Asn Thr Ile Thr Lys Asp Leu
65                  70                  75                  80

Ile Gly Asn Thr Trp Asn Ile Ile Ser Gly Ile Thr Val Ala Phe Val
                85                  90                  95

Leu Tyr Ile Leu Thr Tyr Ala Tyr Ile Ser Ala Asn Gly Ala Ile Ile
            100                 105                 110

Ser Glu Thr Ile Ser Met Asn Leu Gly Tyr His Ala Asn Pro Arg Ile
        115                 120                 125

Val Gly Ile Cys Thr Ala Ile Phe Val Ala Ser Val Leu Trp Ile Ser
    130                 135                 140

Ser Leu Ala Ala Ser Arg Ile Thr Ser Leu Phe Leu Gly Leu Lys Ile
145                 150                 155                 160

Ile Ser Phe Val Ile Val Phe Gly Ser Phe Phe His Val Asp Tyr
                165                 170                 175
```

```
Ser Ile Leu Arg Asp Ala Thr Ser Thr Thr Ala Gly Thr Ser Tyr Phe
            180                 185                 190

Pro Tyr Ile Phe Met Ala Leu Pro Val Cys Leu Ala Ser Phe Gly Phe
        195                 200                 205

His Gly Asn Ile Pro Ser Leu Ile Ile Cys Tyr Gly Lys Arg Lys Asp
    210                 215                 220

Lys Leu Ile Lys Ser Val Val Phe Gly Ser Leu Ala Leu Val Ile
225                 230                 235                 240

Tyr Leu Phe Trp Leu Tyr Cys Thr Met Gly Asn Ile Pro Arg Glu Ser
                245                 250                 255

Phe Lys Ala Ile Ile Ser Ser Gly Gly Asn Val Asp Ser Leu Val Lys
            260                 265                 270

Ser Phe Leu Gly Thr Lys Gln His Gly Ile Ile Glu Phe Cys Leu Leu
        275                 280                 285

Val Phe Ser Asn Leu Ala Val Ala Ser Ser Phe Phe Gly Val Thr Leu
    290                 295                 300

Gly Leu Phe Asp Tyr Leu Ala Asp Leu Phe Lys Ile Asp Asn Ser His
305                 310                 315                 320

Gly Gly Arg Phe Lys Thr Val Leu Leu Thr Phe Leu Pro Pro Ala Leu
                325                 330                 335

Leu Tyr Leu Ile Phe Pro Asn Gly Phe Ile Tyr Gly Ile Gly Gly Ala
            340                 345                 350

Gly Leu Cys Ala Thr Ile Trp Ala Val Ile Pro Ala Val Leu Ala
        355                 360                 365

Ile Lys Ala Arg Lys Lys Phe Pro Asn Gln Met Phe Thr Val Trp Gly
    370                 375                 380

Gly Asn Leu Ile Pro Ala Ile Val Ile Leu Phe Gly Ile Thr Val Ile
385                 390                 395                 400

Leu Cys Trp Phe Gly Asn Val Phe Asn Val Leu Pro Lys Phe Gly
                405                 410                 415

<210> SEQ ID NO 14
<211> LENGTH: 1248
<212> TYPE: DNA
<213> ORGANISM: Escherichia coli
<220> FEATURE:
<221> NAME/KEY: gene
<222> LOCATION: (1)..(1248)
<223> OTHER INFORMATION: tnaB

<400> SEQUENCE: 14
atgactgatc aagctgaaaa aaagcactct gcattttggg gtgttatggt tatagcaggt      60
acagtaattg gtggaggtat gtttgcttta cctgttgatc ttgccggtgc ctggtttttc     120
tggggtgcct ttatccttat cattgcctgg ttttcaatgc ttcattccgg gttattgtta     180
ttagaagcaa atttaaatta tcctgtcggc tccagtttta acaccatcac caaagattta     240
atcggtaaca cctggaacat tatcagcggt attaccgttg ccttcgttct ctatatcctc     300
acttatgcct atatctctgc taatggtgcg atcattagtg aaacgatatc aatgaatttg     360
ggctatcacg ctaatccacg tattgtcggg atctgcacag ccattttcgt tgccagcgta     420
ttgtggataa gttcgttagc cgccagtcgc attacctcat tgttcctcgg gctgaagatt     480
atctcctttg tgatcgtgtt tggttctttc ttcttccatg tcgattactc catcctgcgc     540
gatgccacca gcaccactgc gggaacgtct tacttcccgt atatcttctat ggctttgccg     600 gtgtgtctgg cgtcatttgg tttccacggc aatattccca gcctgattat tgctatgga      660
```

| | |
|---|---|
| aaacgcaaag ataagttaat caaaagcgtg gtatttggtt cgctgctggc gctggtgatt | 720 |
| tatctcttct ggctctattg cacgatgggg aatattccgc gcgaaagctt taaggcgata | 780 |
| atctcctcag gcggcaacgt tgattcgctg gtgaaatcgt tcctcggcac caaacagcac | 840 |
| ggcattatcg agttttgcct gctggtgttc tctaacttag ctgttgccag ttcgttcttt | 900 |
| ggtgtcacgc tggggttgtt cgattatctg gcggacctgt taagattga taactcccac | 960 |
| ggcgggcgtt tcaaaaccgt gctgttaacc ttcctgccac ctgcgttgtt gtatctgatc | 1020 |
| ttcccgaacg gctttattta cgggatcggc ggtgccgggc tgtgcgccac catctgggcg | 1080 |
| gtcattattc ccgcagtgct tgcaatcaaa gctcgcaaga agtttcccaa tcagatgttc | 1140 |
| acggtctggg gcggcaatct tattccggcg attgtcattc tctttggtat aaccgtgatt | 1200 |
| ttgtgctggt tcggcaacgt ctttaacgtg ttacctaaat ttggctaa | 1248 |

<210> SEQ ID NO 15
<211> LENGTH: 11155
<212> TYPE: DNA
<213> ORGANISM: Artificial Sequence
<220> FEATURE:
<223> OTHER INFORMATION: pCL1920_Ptrc_trpO

<400> SEQUENCE: 15

| | |
|---|---|
| cccgtcttac tgtcgggaat tcgcgttggc cgattcatta atgcagctgg cacgacaggt | 60 |
| ttcccgactg gaaagcgggc agtgagcgca acgcaattaa tgtgagttag ctcactcatt | 120 |
| aggcacccca ggctttacac tttatgcttc cggctcgtat gttgtgtgga attgtgagcg | 180 |
| gataacaatt tcacacagga aacagctatg accatgatta cgccaagctt gctgttgaca | 240 |
| attaatcatc cggctcgtat aatgtgtgga attgtgagcg gataacaatt tcacacagga | 300 |
| aacagctgca gatgcaaaca caaaaaccga ctctcgaact gctaacctgc gaaggcgctt | 360 |
| atcgcgacaa tcccaccgcg ctttttcacc agttgtgtgg ggatcgtccg gcaacgctgc | 420 |
| tgctggaatc gcagatatc gacagcaaag atgatttaaa aagcctgctg ctggtagaca | 480 |
| gtgcgctgcg cattacagct ttaggtgaca ctgtcacaat ccaggcactt tccggcaacg | 540 |
| gcgaagccct cctggcacta ctggataacg ccctgcctgc gggtgtggaa agtgaacaat | 600 |
| caccaaactg ccgtgtgctg cgcttccccc ctgtcagtcc actgctggat gaagacgccc | 660 |
| gcttatgctc cctttcggtt tttgacgctt tccgttattt gcagaatctg ttgaatgtac | 720 |
| cgaaggaaga acgagaagcc atgttcttcg gcggcctgtt ctcttatgac cttgtggcgg | 780 |
| gatttgaaga tttaccgcaa ctgtcagcgg aaaataactg ccctgatttc tgtttttatc | 840 |
| tcgctgaaac gctgatggtg attgaccatc agaaaaaaag cacccgtatt caggccagcc | 900 |
| tgtttgctcc gaatgaagaa gaaaacaac gtctcactgc tcgcctgaac gaactacgtc | 960 |
| agcaactgac cgaagccgcg ccgccgctgc cagtggtttc cgtgccgcat atgcgttgtg | 1020 |
| aatgtaatca gagcgatgaa gagttcggtg gcgtagtgcg tttgttgcaa aaagcgattc | 1080 |
| gcgctggaga aattttccag gtggtgccat ctcgccgttt ctctctgccc tgcccgtcac | 1140 |
| cgctggcggc ctattacgtg ctgaaaaaga gtaatccag cccgtacatg tttttatgc | 1200 |
| aggataatga tttcacccta tttggcgcgt cgccggaaag ctcgctcaag tatgatgcca | 1260 |
| ccagccgcca gattgagatc tacccgattg ccggaacacg cccacgcggt cgtcgcgccg | 1320 |
| atggttcact ggacagagat ctcgacagcc gtattgaact ggaaatgcgt accgatcata | 1380 |
| aagagctgtc tgaacatctg atgctggttg atctcgcccg taatgatctg gcacgcattt | 1440 |
| gcacccccgg cagccgctac gtcgccgatc tcaccaaagt tgaccgttat tcctatgtga | 1500 |

-continued

```
tgcacctcgt ctctcgcgta gtcggcgaac tgcgtcacga tcttgacgcc ctgcacgctt   1560
atcgcgcctg tatgaatatg gggacgttaa gcggtgcgcc gaaagtacgc gctatgcagt   1620
taattgccga ggcggaaggt cgtcgccgcg gcagctacgg cggcgcggta ggttatttca   1680
ccgcgcatgg cgatctcgac acctgcattg tgatccgctc ggcgctggtg gaaaacggta   1740
tcgccaccgt gcaagcgggt gctggtgtag tccttgattc tgttccgcag tcggaagccg   1800
acgaaacccg taacaaagcc cgcgctgtac tgcgcgctat tgccaccgcg catcatgcac   1860
aggagacttt ctgatggctg acattctgct gctcgataat atcgactctt ttacgtacaa   1920
cctggcagat cagttgcgca gcaatgggca taacgtggtg atttaccgca accatattcc   1980
ggcgcaaacc ttaattgaac gcctggcgac catgagcaat ccggtgctga tgctttctcc   2040
tggcccggt gtgccgagcg aagccggttg tatgccggaa ctcctcaccc gcttgcgtgg    2100
caagctgccc attattggca tttgcctcgg acatcaggcg attgtcgaag cttacggggg   2160
ctatgtcggt caggcgggcg aaattctcca cggtaaagcc tccagcattg aacatgacgg   2220
tcaggcgatg tttgccggat taacaaaccc gctgccggtg gcgcgttatc actcgctggt   2280
tggcagtaac attccggccg gtttaaccat caacgcccat tttaatggca tggtgatggc   2340
agtacgtcac gatgcggatc gcgtttgtgg attccagttc catccggaat ccattctcac   2400
cacccagggc gctcgcctgc tggaacaaac gctggcctgg gcgcagcaga actagagcc    2460
agccaacacg ctgcaaccga ttctggaaaa actgtatcag gcgcagacgc ttagccaaca   2520
agaaagccac cagctgtttt cagcggtggt gcgtggcgag ctgaagccgg aacaactggc   2580
ggcggcgctg gtgagcatga aaattcgcgg tgagcacccg aacgagatcg ccggggcagc   2640
aaccgcgcta ctggaaaacg cagcgccgtt cccgcgcccg gattatctgt ttgctgatat   2700
cgtcggtact ggcggtgacg gcagcaacag tatcaatatt tctaccgcca gtgcgtttgt   2760
cgccgcggcc tgtgggctga agtggcgaa acacggcaac cgtagcgtct ccagtaaatc    2820
tggttcgtcc gatctgctgg cggcgttcgg tattaatctt gatatgaacg ccgataaatc   2880
gcgccaggcg ctggatgagt taggtgtatg tttcctcttt gcgccgaagt atcacaccgg   2940
attccgccac gcgatgccgg ttcgccagca actgaaaacc cgcaccctgt caatgtgct    3000
ggggccattg attaacccgg cgcatccgcc gctggcgtta attggtgttt atagtccgga   3060
actggtgctg ccgattgccg aaaccttgcg cgtgctgggg tatcaacgcg cggcggtggt   3120
gcacagcggc gggatggatg aagtttcatt acacgcgccg acaatcgttg ccgaactgca   3180
tgacggcgaa attaaaagct atcagctcac cgcagaagac tttggcctga cacctacca    3240
ccaggagcaa ctgcaggcg gaacaccgga agaaaaccgt gacattttaa cacgtttgtt    3300
acaaggtaaa ggcgacgccg cccatgaagc agccgtcgct gcgaacgtcg ccatgttaat   3360
gcgcctgcat ggccatgaag atctgcaagc caatgcgcaa accgttcttg aggtactgcg   3420
cagtggttcc gcttacgaca gagtcaccgc actggcggca cgagggtaaa tgatgcaaac   3480
cgttttagcg aaaatcgtcg cagacaaggc gatttgggta gaagcccgca acagcagca    3540
accgctggcc agttttcaga atgaggttca gccgagcacg cgacatttt atgatgcgct    3600
acagggtgcg cgcacggcgt ttattctgga gtgcaagaaa gcgtcgccgt caaaaggcgt   3660
gatccgtgat gatttcgatc cagcacgcat tgccgccatt tataaacatt acgcttcggc   3720
aatttcggtg ctgactgatg agaaatattt tcaggggagc tttaatttcc tccccatcgt   3780
cagccaaatc gccccgcagc cgattttatg taaagacttc attatcgacc cttaccagat   3840
ctatctggcg cgctattacc aggccgatgc ctgcttatta atgctttcag tactggatga   3900
```

-continued

| | | | | | |
|---|---|---|---|---|---|
| cgaccaatat | cgccagcttg | ccgccgtcgc | tcacagtctg | gagatggggg | tgctgaccga | 3960 |
| agtcagtaat | gaagaggaac | aggagcgcgc | cattgcattg | ggagcaaagg | tcgttggcat | 4020 |
| caacaaccgc | gatctgcgtg | atttgtcgat | tgatctcaac | cgtacccgcg | agcttgcgcc | 4080 |
| gaaactgggg | cacaacgtga | cggtaatcag | cgaatccggc | atcaatactt | acgctcaggt | 4140 |
| gcgcgagtta | agccacttcg | ctaacggttt | tctgattggt | tcggcgttga | tggcccatga | 4200 |
| cgatttgcac | gccgccgtgc | gccgggtgtt | gctgggtgag | aataaagtat | gtggcctgac | 4260 |
| gcgtgggcaa | gatgctaaag | cagcttatga | cgcgggcgcg | atttacggtg | ggttgatttt | 4320 |
| tgttgcgaca | tcaccgcgtt | gcgtcaacgt | tgaacaggcg | caggaagtga | tggctgcggc | 4380 |
| accgttgcag | tatgttggcg | tgttccgcaa | tcacgatatt | gccgatgtgg | tggacaaagc | 4440 |
| taaggtgtta | tcgctggcgg | cagtgcaact | gcatggtaat | gaagaacagc | tgtatatcga | 4500 |
| tacgctgcgt | gaagctctgc | cagcacatgt | tgccatctgg | aaagcattaa | gcgtcggtga | 4560 |
| aaccctgccc | gcccgcgagt | ttcagcacgt | tgataaatat | gttttagaca | acggccaggg | 4620 |
| tggaagcggg | caacgttttg | actggtcact | attaaatggt | caatcgcttg | caacgttct | 4680 |
| gctggcgggg | ggcttaggcg | cagataactg | cgtggaagcg | gcacaaaccg | gctgcgccgg | 4740 |
| acttgatttt | aattctgctg | tagagtcgca | accgggcatc | aaagacgcac | gtcttttggc | 4800 |
| ctcggttttc | cagacgctgc | gcgcatatta | aggaaggaa | caatgacaac | attacttaac | 4860 |
| ccctattttg | gtgagtttgg | cggcatgtac | gtgccacaaa | tcctgatgcc | tgctctgcgc | 4920 |
| cagctggaag | aagcttttgt | cagtgcgcaa | aaagatcctg | aatttcaggc | tcagttcaac | 4980 |
| gacctgctga | aaaactatgc | cgggcgtcca | accgcgctga | ccaaatgcca | gaacattaca | 5040 |
| gccgggacga | acaccacgct | gtatctcaag | cgtgaagatt | tgctgcacgg | cggcgcgcat | 5100 |
| aaaactaacc | aggtgctggg | gcaggcgttg | ctggcgaagc | ggatgggtaa | aaccgaaatc | 5160 |
| atcgccgaaa | ccggtgccgg | tcagcatggc | gtggcgtcgg | cccttgccag | cgccctgctc | 5220 |
| ggcctgaaat | gccgtattta | tatgggtgcc | aaagacttg | aacgccagtc | gcctaacgtt | 5280 |
| tttcgtatgc | gcttaatggg | tgcggaagtg | atcccggtgc | atagcggttc | cgcgacgctg | 5340 |
| aaagatgcct | gtaacgaggc | gctgcgcgac | tggtccggta | gttacgaaac | cgcgcactat | 5400 |
| atgctgggca | ccgcagctgg | cccgcatcct | tatccgacca | ttgtgcgtga | gtttcagcgg | 5460 |
| atgattggcg | aagaaccaa | agcgcagatt | ctggaaagag | aaggtcgcct | gccggatgcc | 5520 |
| gttatcgcct | gtgttggcgg | cggttcgaat | gccatcggca | tgtttgctga | tttcatcaat | 5580 |
| gaaaccaacg | tcggcctgat | tggtgtggag | ccaggtggtc | acggtatcga | aactggcgag | 5640 |
| cacggcgcac | cgctaaaaca | tggtcgcgtg | ggtatctatt | tcggtatgaa | agcgccgatg | 5700 |
| atgcaaaccg | aagacgggca | gattgaagaa | tcttactcca | tctccgccgg | actggatttc | 5760 |
| ccgtctgtcg | gcccacaaca | cgcgtatctt | aacagcactg | gacgcgctga | ttacgtgtct | 5820 |
| attaccgatg | atgaagccct | tgaagccttc | aaaacgctgt | gcctgcacga | agggatcatc | 5880 |
| ccggcgctgg | aatcctccca | cgccctggcc | catgcgttga | aaatgatgcg | cgaaaacccg | 5940 |
| gataaagagc | agctactggt | ggttaacctt | tccggtcgcg | gcgataaaga | catcttcacc | 6000 |
| gttcacgata | ttttgaaagc | acgaggggaa | atctgatgga | acgctacgaa | tctctgtttg | 6060 |
| cccagttgaa | ggagcgcaaa | gaaggcgcat | tcgttccttt | cgtcacgctc | ggtgatccgg | 6120 |
| gcattgagca | gtcattgaaa | attatcgata | cgctaattga | agccggtgct | gacgcgctgg | 6180 |
| agttaggtat | ccccttctcc | gacccactgg | cggatggccc | gacgattcaa | aacgccactc | 6240 |
| tgcgcgcctt | tgcggcaggt | gtgactccgg | cacaatgttt | tgaaatgctg | gcactgattc | 6300 |

```
gccagaaaca cccgaccatt cccattggcc tgttgatgta tgccaatctg gtgtttaaca      6360
aaggcattga tgagttttat gcccagtgcg aaaaagtcgg cgtcgattcg gtgctggttg      6420
ccgatgtgcc agttgaagag tccgcgccct tccgccaggc cgcgttgcgt cataatgtcg      6480
cacctatctt catctgcccg ccaaatgccg atgacgacct gctgcgccag atagcctctt      6540
acggtcgtgg ttacacctat ttgctgtcac gagcaggcgt gaccggcgca gaaaaccgcg      6600
ccgcgttacc cctcaatcat ctggttgcga agctgaaaga gtacaacgct gcacctccat      6660
tgcagggatt tggtatttcc gccccggatc aggtaaaagc agcgattgat gcaggagctg      6720
cgggcgcgat ttctggttcg gccattgtta aaatcatcga gcaacatatt aatgagccag      6780
agaaaatgct ggcggcactg aaagtttttg tacaaccgat gaaagcggcg acgcgcagtt      6840
aactgcaggt cgactctaga ggatccccgg gtaccgagct cgaattcact ggccgtcgtt      6900
ttacaacgtc gtgactggga aaaccctggc gttacccaac ttaatcgcct tgcagcacat      6960
ccccctttcg ccagctggcg taatagcgaa gaggcccgca ccgatcgccc ttcccaacag      7020
ttgcgcagcc tgaatggcga atggcgcctg atgcggtatt ttctccttac gcatctgtgc      7080
ggtatttcac accgcatatg gtgcactctc agtacaatct gctctgatgc cgcatagtta      7140
agccagcccc gacacccgcc aacacccgct gacgagctta gtaaagccct cgctagattt      7200
taatgcggat gttgcgatta cttcgccaac tattgcgata caagaaaaa gccagccttt      7260 catgatatat ctcccaattt gtgtagggct tattatgcac gcttaaaaat aataaaagca      7320
gacttgacct gatagtttgg ctgtgagcaa ttatgtgctt agtgcatcta acgcttgagt      7380
taagccgcgc cgcgaagcgg cgtcggcttg aacgaattgt tagacattat ttgccgacta      7440
ccttggtgat ctcgcctttc acgtagtgga caaattcttc caactgatct gcgcgcgagg      7500
ccaagcgatc ttcttcttgt ccaagataag cctgtctagc ttcaagtatg acgggctgat      7560
actgggccgg caggcgctcc attgcccagt cggcagcgac atccttcggc gcgattttgc      7620
cggttactgc gctgtaccaa atgcgggaca acgtaagcac tacatttcgc tcatcgccag      7680
cccagtcggg cggcgagttc catagcgtta aggtttcatt tagcgcctca aatagatcct      7740
gttcaggaac cggatcaaag agttcctccg ccgctggacc taccaaggca acgctatgtt      7800
ctcttgcttt tgtcagcaag atagccagat caatgtcgat cgtggctggc tcgaagatac      7860
ctgcaagaat gtcattgcgc tgccattctc caaattgcag ttcgcgctta gctggataac      7920
gccacggaat gatgtcgtcg tgcacaacaa tggtgacttc tacagcgcgg agaatctcgc      7980
tctctccagg ggaagccgaa gtttccaaaa ggtcgttgat caaagctcgc cgcgttgttt      8040
catcaagcct tacggtcacc gtaaccagca aatcaatatc actgtgtggc ttcaggccgc      8100
catccactgc ggagccgtac aaatgtacgg ccagcaacgt cggttcgaga tggcgctcga      8160
tgacgccaac tacctctgat agttgagtcg atacttcggc gatcaccgct tccctcatga      8220
tgtttaactt tgttttaggg cgactgccct gctgcgtaac atcgttgctg ctccataaca      8280
tcaaacatcg acccacggcg taacgcgctt gctgcttgga tgcccgaggc atagactgta      8340
ccccaaaaaa acagtcataa caagccatga aaaccgccac tgcgccgtta ccaccgctgc      8400
gttcggtcaa ggttctggac cagttgcgtg agcgcatacg ctacttgcat tacagcttac      8460
gaaccgaaca ggcttatgtc cactgggttc gtgccttcat ccgtttccac ggtgtgcgtc      8520
acccggcaac cttgggcagc agcgaagtcg aggcatttct gtcctggctg gcgaacgagc      8580
gcaaggtttc ggtctccacg catcgtcagg cattggcggc cttgctgttc ttctacggca      8640
aggtgctgtg cacggatctg ccctggcttc aggagatcgg aagacctcgg ccgtcgcggc      8700
```

```
gcttgccggt ggtgctgacc ccggatgaag tggttcgcat cctcggtttt ctggaaggcg    8760
agcatcgttt gttcgcccag cttctgtatg aacgggcat  gcggatcagt gagggtttgc    8820
aactgcgggt caaggatctg gatttcgatc acggcacgat catcgtgcgg gagggcaagg    8880
gctccaagga tcgggccttg atgttacccg agagcttggc acccagcctg cgcgagcagg    8940
ggaattaatt cccacgggtt ttgctgcccg caaacgggct gttctggtgt tgctagtttg    9000
ttatcagaat cgcagatccg gcttcagccg gtttgccggc tgaaagcgct atttcttcca    9060
gaattgccat gattttttcc ccacgggagg cgtcactggc tcccgtgttg tcggcagctt    9120
tgattcgata agcagcatcg cctgtttcag gctgtctatg tgtgactgtt gagctgtaac    9180
aagttgtctc aggtgttcaa tttcatgttc tagttgcttt gttttactgg tttcacctgt    9240
tctattaggt gttacatgct gttcatctgt tacattgtcg atctgttcat ggtgaacagc    9300
tttgaatgca ccaaaaactc gtaaaagctc tgatgtatct atctttttta caccgttttc    9360
atctgtgcat atggacagtt ttcccttga tatgtaacgg tgaacagttg ttctactttt     9420
gtttgttagt cttgatgctt cactgataga tacaagagcc ataagaacct cagatccttc    9480
cgtatttagc cagtatgttc tctagtgtgg ttcgttgttt ttgcgtgagc catgagaacg    9540
aaccattgag atcatactta ctttgcatgt cactcaaaaa ttttgcctca aaactggtga    9600
gctgaatttt tgcagttaaa gcatcgtgta gtgtttttct tagtccgtta tgtaggtagg    9660
aatctgatgt aatggttgtt ggtattttgt caccattcat ttttatctgg ttgttctcaa    9720
gttcggttac gagatccatt tgtctatcta gttcaacttg gaaaatcaac gtatcagtcg    9780
ggcggcctcg cttatcaacc accaatttca tattgctgta agtgtttaaa tctttactta    9840
ttggtttcaa aacccattgg ttaagccttt taaactcatg gtagttattt tcaagcatta    9900
acatgaactt aaattcatca aggctaatct ctatatttgc cttgtgagtt ttcttttgtg    9960
ttagttcttt taataaccac tcataaatcc tcatagagta tttgttttca aaagacttaa    10020
catgttccag attatatttt atgaattttt ttaactggaa aagataaggc aatatctctt    10080
cactaaaaac taattctaat ttttcgcttg agaacttggc atagtttgtc cactggaaaa    10140
tctcaaagcc tttaaccaaa ggattcctga tttccacagt tctcgtcatc agctctctgg    10200
ttgctttagc taatacacca taagcatttt ccctactgat gttcatcatc tgagcgtatt    10260
ggttataagt gaacgatacc gtccgttctt tccttgtagg gttttcaatc gtggggttga    10320
gtagtgccac acagcataaa attagcttgg tttcatgctc cgttaagtca tagcgactaa    10380
tcgctagttc atttgctttg aaaacaacta attcagacat acatctcaat tggtctaggt    10440
gattttaatc actataccaa ttgagatggg ctagtcaatg ataattacta gtccttttcc    10500
tttgagttgt gggtatctgt aaattctgct agacctttgc tggaaaactt gtaaattctg    10560
ctagaccctc tgtaaattcc gctagacctt tgtgtgtttt ttttgtttat attcaagtgg    10620
ttataattta tagaataaag aaagaataaa aaagataaa  agaatagat  cccagccctg    10680 tgtataactc actactttag tcagttccgc agtattacaa aaggatgtcg caaacgctgt    10740
ttgctcctct acaaaacaga ccttaaaacc ctaaaggctt aagtagcacc ctcgcaagct    10800
cgggcaaatc gctgaatatt ccttttgtct ccgaccatca ggcacctgag tcgctgtctt    10860
tttcgtgaca ttcagttcgc tgcgctcacg gctctggcag tgaatggggg taaatggcac    10920
tacaggcgcc ttttatggat tcatgcaagg aaactaccca taatacaaga aaagcccgtc    10980
acgggcttct cagggcgttt tatggcgggt ctgctatgtg gtgctatctg acttttttgct   11040
```

-continued

```
gttcagcagt tcctgccctc tgattttcca gtctgaccac ttcggattat cccgtgacag    11100
gtcattcaga ctggctaatg cacccagtaa ggcagcggta tcatcaacag gctta         11155
```

<210> SEQ ID NO 16
<211> LENGTH: 38
<212> TYPE: DNA
<213> ORGANISM: Artificial Sequence
<220> FEATURE:
<223> OTHER INFORMATION: Primer 1

<400> SEQUENCE: 16

```
aggcaacact atgacatcgt gtaggctgga gctgcttc                              38
```

<210> SEQ ID NO 17
<211> LENGTH: 40
<212> TYPE: DNA
<213> ORGANISM: Artificial Sequence
<220> FEATURE:
<223> OTHER INFORMATION: Primer 2

<400> SEQUENCE: 17

```
ggtcgccatt aacaacgtgg catatgaata tcctccttag                            40
```

<210> SEQ ID NO 18
<211> LENGTH: 19
<212> TYPE: DNA
<213> ORGANISM: Artificial Sequence
<220> FEATURE:
<223> OTHER INFORMATION: Primer 3

<400> SEQUENCE: 18

```
tattgagtgt atcgccaac                                                   19
```

<210> SEQ ID NO 19
<211> LENGTH: 18
<212> TYPE: DNA
<213> ORGANISM: Artificial Sequence
<220> FEATURE:
<223> OTHER INFORMATION: Primer 4

<400> SEQUENCE: 19

```
cgatgtcata gtgttgcc                                                    18
```

<210> SEQ ID NO 20
<211> LENGTH: 20
<212> TYPE: DNA
<213> ORGANISM: Artificial Sequence
<220> FEATURE:
<223> OTHER INFORMATION: Primer 5

<400> SEQUENCE: 20

```
ccacgttgtt aatggcgacc                                                  20
```

<210> SEQ ID NO 21
<211> LENGTH: 20
<212> TYPE: DNA
<213> ORGANISM: Artificial Sequence
<220> FEATURE:
<223> OTHER INFORMATION: Primer 6

<400> SEQUENCE: 21

```
ttcattgaac gggtgatttc                                                  20
```

```
<210> SEQ ID NO 22
<211> LENGTH: 70
<212> TYPE: DNA
<213> ORGANISM: Artificial Sequence
<220> FEATURE:
<223> OTHER INFORMATION: Primer 7

<400> SEQUENCE: 22
tccgcacgtt tatgatatgc tatcgtactc tttagcgagt acaaccgggg gtgtaggctg    60
gagctgcttc                                                          70

<210> SEQ ID NO 23
<211> LENGTH: 70
<212> TYPE: DNA
<213> ORGANISM: Artificial Sequence
<220> FEATURE:
<223> OTHER INFORMATION: Primer 8

<400> SEQUENCE: 23
gccacgtctt atcaggccta caaaatcaat cgcttttcag caacacctct catatgaata    60
tcctccttag                                                          70

<210> SEQ ID NO 24
<211> LENGTH: 20
<212> TYPE: DNA
<213> ORGANISM: Artificial Sequence
<220> FEATURE:
<223> OTHER INFORMATION: Primer 9

<400> SEQUENCE: 24
gcgccgggcg tatcgacgca                                               20

<210> SEQ ID NO 25
<211> LENGTH: 20
<212> TYPE: DNA
<213> ORGANISM: Artificial Sequence
<220> FEATURE:
<223> OTHER INFORMATION: Primer 10

<400> SEQUENCE: 25
gcatatcata aacgtgcgga                                               20

<210> SEQ ID NO 26
<211> LENGTH: 20
<212> TYPE: DNA
<213> ORGANISM: Artificial Sequence
<220> FEATURE:
<223> OTHER INFORMATION: Primer 11

<400> SEQUENCE: 26
tgtaggcctg ataagacgtg                                               20

<210> SEQ ID NO 27
<211> LENGTH: 20
<212> TYPE: DNA
<213> ORGANISM: Artificial Sequence
<220> FEATURE:
<223> OTHER INFORMATION: Primer 12

<400> SEQUENCE: 27 aagggggcgat cggcgtgttt                                              20
```

```
<210> SEQ ID NO 28
<211> LENGTH: 70
<212> TYPE: DNA
<213> ORGANISM: Artificial Sequence
<220> FEATURE:
<223> OTHER INFORMATION: Primer 13

<400> SEQUENCE: 28
atggcaacac taaccaccac ccaaacgtca ccgtcgctgc ttggcggcgt gtgtaggctg      60
gagctgcttc                                                            70

<210> SEQ ID NO 29
<211> LENGTH: 70
<212> TYPE: DNA
<213> ORGANISM: Artificial Sequence
<220> FEATURE:
<223> OTHER INFORMATION: Primer 14

<400> SEQUENCE: 29
ttactgatac accggcagta aattaaagct cgataaaata tgcaccagtg catatgaata      60
tcctccttag                                                            70

<210> SEQ ID NO 30
<211> LENGTH: 20
<212> TYPE: DNA
<213> ORGANISM: Artificial Sequence
<220> FEATURE:
<223> OTHER INFORMATION: Primer 15

<400> SEQUENCE: 30
gcagccgtta cattggtaac                                                 20

<210> SEQ ID NO 31
<211> LENGTH: 20
<212> TYPE: DNA
<213> ORGANISM: Artificial Sequence
<220> FEATURE:
<223> OTHER INFORMATION: Primer 16

<400> SEQUENCE: 31
gtggtggtta gtgttgccat                                                 20

<210> SEQ ID NO 32
<211> LENGTH: 20
<212> TYPE: DNA
<213> ORGANISM: Artificial Sequence
<220> FEATURE:
<223> OTHER INFORMATION: Primer 17

<400> SEQUENCE: 32
tactgccggt gtatcagtaa                                                 20

<210> SEQ ID NO 33
<211> LENGTH: 20
<212> TYPE: DNA
<213> ORGANISM: Artificial Sequence
<220> FEATURE:
<223> OTHER INFORMATION: Primer 18

<400> SEQUENCE: 33
tcaaaccgtc agcacggctg                                                 20
```

```
<210> SEQ ID NO 34
<211> LENGTH: 70
<212> TYPE: DNA
<213> ORGANISM: Artificial Sequence
<220> FEATURE:
<223> OTHER INFORMATION: Primer 19

<400> SEQUENCE: 34
atgaaggatt atgtaatgga aaactttaaa catctccctg aaccgttccg gtgtaggctg      60
gagctgcttc                                                            70

<210> SEQ ID NO 35
<211> LENGTH: 70
<212> TYPE: DNA
<213> ORGANISM: Artificial Sequence
<220> FEATURE:
<223> OTHER INFORMATION: Primer 20

<400> SEQUENCE: 35
ttagccaaat ttaggtaaca cgttaaagac gttgccgaac cagcacaaaa catatgaata      60
tcctccttag                                                            70

<210> SEQ ID NO 36
<211> LENGTH: 21
<212> TYPE: DNA
<213> ORGANISM: Artificial Sequence
<220> FEATURE:
<223> OTHER INFORMATION: Primer 21

<400> SEQUENCE: 36
ttaagcgaaa tcaccgggga a                                               21

<210> SEQ ID NO 37
<211> LENGTH: 18
<212> TYPE: DNA
<213> ORGANISM: Artificial Sequence
<220> FEATURE:
<223> OTHER INFORMATION: Primer 22

<400> SEQUENCE: 37
atgtccgagc actggcgc                                                   18

<210> SEQ ID NO 38
<211> LENGTH: 28
<212> TYPE: DNA
<213> ORGANISM: Artificial Sequence
<220> FEATURE:
<223> OTHER INFORMATION: Primer 23

<400> SEQUENCE: 38
cccaagcttg ctgttgacaa ttaatcat                                        28

<210> SEQ ID NO 39
<211> LENGTH: 28
<212> TYPE: DNA
<213> ORGANISM: Artificial Sequence
<220> FEATURE:
<223> OTHER INFORMATION: Primer 24

<400> SEQUENCE: 39
aaaactgcag ctgtttcctg tgtgaaat                                        28
```

```
<210> SEQ ID NO 40
<211> LENGTH: 31
<212> TYPE: DNA
<213> ORGANISM: Artificial Sequence
<220> FEATURE:
<223> OTHER INFORMATION: Primer 25

<400> SEQUENCE: 40
aaaactgcag atgcaaacac aaaaaccgac t                                      31

<210> SEQ ID NO 41
<211> LENGTH: 32
<212> TYPE: DNA
<213> ORGANISM: Artificial Sequence
<220> FEATURE:
<223> OTHER INFORMATION: Primer 26

<400> SEQUENCE: 41
aaaactgcag ttaactgcgc gtcgccgctt tc                                     32

<210> SEQ ID NO 42
<211> LENGTH: 70
<212> TYPE: DNA
<213> ORGANISM: Artificial Sequence
<220> FEATURE:
<223> OTHER INFORMATION: Primer 27

<400> SEQUENCE: 42
aaacgcgttg tgaatcatcc tgctctgaca actcaatttc aggagccttt gccgccagct       60
gaagctttac                                                              70

<210> SEQ ID NO 43
<211> LENGTH: 70
<212> TYPE: DNA
<213> ORGANISM: Artificial Sequence
<220> FEATURE:
<223> OTHER INFORMATION: Primer 28

<400> SEQUENCE: 43
acagcacgct tttcagcgcc aggtagtcac ggtagttagc cggagaaata tagtggatct       60
gatgggtacc                                                              70

<210> SEQ ID NO 44
<211> LENGTH: 70
<212> TYPE: DNA
<213> ORGANISM: Artificial Sequence
<220> FEATURE:
<223> OTHER INFORMATION: Primer 29

<400> SEQUENCE: 44
tgccctatga gctccggtta caggcgtttc agtcataaat cctctgaatg aaacgcgttg       60
tgaatcatcc                                                              70

<210> SEQ ID NO 45
<211> LENGTH: 70
<212> TYPE: DNA
<213> ORGANISM: Artificial Sequence
<220> FEATURE:
<223> OTHER INFORMATION: Primer 30

<400> SEQUENCE: 45
atcgcccgct tccagcgcat ctgccggaac cagccaggaa ccaccgatgc acagcacgct       60
tttcagcgcc                                                              70
```

```
<210> SEQ ID NO 46
<211> LENGTH: 21
<212> TYPE: DNA
<213> ORGANISM: Artificial Sequence
<220> FEATURE:
<223> OTHER INFORMATION: Primer 31

<400> SEQUENCE: 46
catgatcttg cgcagattgt a                                              21

<210> SEQ ID NO 47
<211> LENGTH: 21
<212> TYPE: DNA
<213> ORGANISM: Artificial Sequence
<220> FEATURE:
<223> OTHER INFORMATION: Primer 32

<400> SEQUENCE: 47
catgatcttg cgcagattgt a                                              21
```

MICROORGANISM OF THE GENUS *ESCHERICHIA* PRODUCING L-TRYPTOPHAN AND METHOD FOR PRODUCING L-TRYPTOPHAN USING THE SAME

CROSS-REFERENCES TO RELATED APPLICATIONS

This application is a U.S. national phase application of International PCT Patent Application No. PCT/KR2015/006350, which was filed on Jun. 23, 2015, which claims priority to Korean Patent Application No. 10-2014-0076698, filed Jun. 23, 2014. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_055_00US_ST25.txt. The text file is 55 KB, was created on Dec. 22, 2016, and is being submitted electronically via EFS-Web.

TECHNICAL FIELD

The present application relates to a microorganism of the genus *Escherichia* producing L-tryptophan and a method for producing L-tryptophan using the microorganism.

BACKGROUND ART

L-tryptophan, which is an essential amino acid, has been widely used as a feed additive, etc., and has also been widely used as a raw material for pharmaceutical products such as infusion solutions and health food ingredients. L-tryptophan can be produced by a chemical synthesis method, an enzyme reaction method, a fermentation method, etc., but the direct fermentation method using a microorganism is mostly used at present.

Regarding the direction of developing an L-tryptophan-producing strain, the development was initially progressed by selecting mutations (Korean Patent No. 1987-0001813), or by methods of overcoming the tryptophan feedback inhibition by the enzymes in the biosynthesis pathways along with genetic engineering, or by enhancing enzyme synthesis in metabolic processes such as enhancing the expression of tryptophan biosynthesis enzymes.

Meanwhile, a method for improving L-amino acids using the Entner-Doudoroff pathway was disclosed previously (U.S. Pat. No. 7,432,085). U.S. Pat. No. 7,432,085 relates to a method for improving the production of an L-amino acid produced by a biosynthesis pathway utilizing pyruvic acid as an intermediate, by enhancing the activities of enzymes involved in the Entner-Doudoroff pathway, and specifically, a key feature of the patent is to enhance the activity of 6-phosphogluconate dehydratase or 2-keto-3-deoxy-6-phosphogluconate aldolase.

However, the present inventors have confirmed for the first time that, in the case of L-tryptophan, unlike other L-amino acids, when the activities of 6-phosphogluconate dehydratase and 2-keto-3-deoxy-6-phosphogluconate aldolase in the Entner-Doudoroff pathway are both weakened or inactivated, the ability to produce L-tryptophan can be significantly improved, thereby completing the present invention regarding the microorganism of the genus *Escherichia* with an improved ability of producing L-tryptophan and a method for producing L-tryptophan using the microorganism.

DISCLOSURE

Technical Problem

An object of the present application is to provide a microorganism producing L-tryptophan.

Another object of the present application is to provide a method for effectively producing L-tryptophan using the microorganism producing L-tryptophan.

Technical Solution

In order to achieve the above objects, in an aspect, the present application provides a microorganism of the genus *Escherichia* producing L-tryptophan by weakening or inactivating the activities of endogenous 6-phosphogluconate dehydratase (edd) and 2-keto-3-deoxy-6-phosphogluconate aldolase (eda).

As used herein, the term "L-tryptophan" refers to an aromatic L-amino acid, which is an α-amino acid and an essential amino acid not synthesized in vivo having a chemical formula of $C_{11}H_{12}N_2O_2$.

As used herein, the term "Entner-Doudoroff pathway" refers to a carbon metabolic pathway present in a microorganism of the genus *Escherichia*, which is a pathway catalyzing the conversion of carbon sources introduced to the carbon metabolic pathway into glyceraldehyde-3-phosphate and pyruvate through a serial two-step enzyme reaction by 6-phosphogluconate dehydratase and 2-keto-3-deoxy-6-phosphogluconate aldolase.

As used herein, the term "6-phosphogluconate dehydratase (Edd; EC 4.2.1.12)" refers to an enzyme involved in the Entner-Doudoroff pathway, which catalyzes the reaction of converting 6-phospho-D-gluconate into 2-dihydro-3-deoxy-6-phospho-D-gluconate. Specifically, the enzyme may have an amino acid sequence of SEQ ID NO: 1, but any sequence having the activity of the enzyme may be included without limitation. Additionally, in an exemplary embodiment, the gene encoding the 6-phosphogluconate dehydratase may be represented by the nucleotide sequence of SEQ ID NO: 2, but any sequence encoding the enzyme can be included without limitation.

As used herein, the term "2-keto-3-deoxy-6-phosphogluconate aldolase (Eda; EC 4.1.2.14)" refers to an enzyme involved in the Entner-Doudoroff pathway, which catalyzes the reaction of converting 2-dihydro-3-deoxy-6-phospho-D-gluconate into glyceraldehyde-3-phosphate and pyruvate. Specifically, the enzyme may have an amino acid sequence of SEQ ID NO: 3, but any sequence having the activity of the enzyme may be included without limitation. Additionally, in an exemplary embodiment, the gene encoding the 2-keto-3-deoxy-6-phosphogluconate aldolase may be represented by the nucleotide sequence of SEQ ID NO: 4, but any sequence encoding the enzyme can be included without limitation.

Each of the enzymes described above may include without limitation, in addition to the amino acid sequences represented by SEQ ID NOS: 1 to 3, any amino acid sequence which has a homology of 70% or higher, specifically 80% or higher, more specifically 90% or higher, even more specifically 95% or higher, yet even more specifically 98% or higher, and yet even still more specifically 99% or higher, to each of the above-listed amino acid sequences, as long as the enzyme exhibits an effect substantially the same as or corresponding to each of the enzymes. Additionally, it is obvious that any modified enzyme which has the homology described above and has the effect corresponding to each enzyme can belong to the scope of the present application, although the enzyme may have an amino acid sequence with a partial deletion, modification, substitution, or addition.

Additionally, the genes encoding each of the enzymes may also include without limitation, in addition to the nucleotide sequences represented by SEQ ID NO: 2 or 4, any gene sequence encoding the enzymes, which has a homology of 80% or higher, specifically 90% or higher, more specifically 95% or higher, even more specifically 98% or higher, and yet even more specifically 99% or higher, to each of the above-listed nucleotide sequences, as long as the sequence encodes an enzyme which has an effect substantially the same as or corresponding to each of the enzymes, Additionally, it is obvious that any nucleotide sequence which has the above homologies can belong to the scope of the present application, although the sequence may have a partial deletion, modification, substitution, or addition therein.

As used herein, the term "homology" refers to a percentage of identity between two polynucleotide or polypeptide moieties. Sequence correspondence from one moiety to another may be determined by a known technique in the art. For example, homology may be determined by directly aligning the sequence information (e.g., parameters such as score, identity, and similarity) on two polynucleotide molecules or two polypeptide molecules using a computer program (e.g., BLAST 2.0) that is readily available and capable of aligning sequence information. Additionally, homology may be determined by hybridizing the polynucleotides under the condition for forming a stable double-strand in the homologous regions and then digesting the hybridized strand by a single-strand-specific nuclease to determine the size of digested fragments.

As used herein, the term "endogenous activity" refers to an active state of an enzyme in a microorganism in a natural state or before modification.

As used herein, the term "weakening of the activity of an enzyme compared to its endogenous activity" refers to a concept including a case when there is a decrease in activity of an enzyme in a microorganism compared with that originally possessed in its natural state or before modification, a case when the level of overall protein expression is lower than that of the wild type strain or that of the strain before modification of the microorganism due to inhibition of expression or inhibition of translation of the gene encoding the same, or a combined case thereof.

As used herein, the term "inactivation" refers to a case when the gene encoding an enzyme in a microorganism is not expressed at all and a case when the gene is expressed but exhibits no activity compared to that of the wild type strain or the strain before modification of the microorganism.

The weakening or inactivation of an enzyme activity may be achieved by various methods well-known in the art. Examples of the methods may include a method of substituting the gene encoding the enzyme on the chromosome with a gene mutated so that the enzyme activity can be reduced, including the case when the enzyme activity is eliminated; a method of introducing a modification into the expression control sequence of the gene on the chromosome encoding the enzyme; a method of substituting the expression control sequence of the gene encoding the enzyme with a sequence having weak or no activity; a method of deleting part or the entirety of a gene encoding the enzyme on the chromosome; a method of introducing an antisense oligonucleotide (e.g., antisense RNA), which inhibits the translation from the mRNA into an enzyme by a complementary binding to the transcript of the gene on the chromosome; a method of making the attachment of ribosome impossible by forming a secondary structure by artificially adding a Shine-Dalgarno (SD) sequence and its complementary sequence on the front end of the SD sequence of the gene encoding the enzyme; a method of reverse transcription engineering (RTE), which adds a promoter to be reversely transcribed on the 3' terminus of the open reading frame (ORF) of the corresponding sequence, etc., and may also include a combination thereof, but are not limited thereto.

Specifically, the method of deleting part or the entirety of a gene encoding the enzyme may be performed by substituting a polynucleotide encoding an endogenous target protein within the chromosome with a polynucleotide or a marker gene having a partial deletion in the nucleic acid sequence, using a vector for chromosomal insertion in bacteria. In an exemplary embodiment of the method for deleting part or the entirety of a gene, the gene may be deleted by homologous recombination.

As used herein, the term "part", although it may vary depending on the kinds of polynucleotides, may specifically refer to 1 nucleotide to 300 nucleotides, more specifically 1 nucleotide to 100 nucleotides, and even more specifically 1 nucleotide to 50 nucleotides, but is not particularly limited thereto.

As used herein, the term "homologous recombination" refers to genetic recombination that occurs via crossover at genetic chain loci having mutual homology.

Specifically, the expression control sequence may be modified by inducing a modification of the expression control sequence via deletion, insertion, non-conservative or conservative substitution, or a combination thereof in the nucleic acid sequence of the expression control sequence; or by substituting with a weaker promoter, etc. The expression control sequence may include a promoter, an operator sequence, a sequence encoding a ribosome-binding region, and sequences controlling the termination of transcription and translation.

Furthermore, the gene sequence on the chromosome may be modified by inducing a modification in the sequence by deletion, insertion, non-conservative or conservative substitution, or a combination thereof in the gene sequence for further weakening the enzyme activity; or by substituting with a gene sequence which was improved to have weaker activity or a gene sequence which was improved to have no activity.

In an exemplary embodiment of the present application, it was confirmed that the weakening or inactivation of the activity may be performed by at least one mutation method selected from the group consisting of an insertion mutation performed by inserting at least one base pair into the gene encoding the 6-phosphogluconate dehydratase and into the gene encoding the 2-keto-3-deoxy-6-phosphogluconate aldolase; a deletion mutation performed by having a deletion in at least one base pair within the gene; and a transition or transversion mutation of a base pair performed by introducing a non-sense codon or different codon into the gene.

In the present application, the microorganism of the genus *Escherichia* may be specifically *Escherichia coli*, but is not limited thereto.

Specifically, the parent strain of the microorganism of the genus *Escherichia* producing L-tryptophan by weakening or inactivating the activities of edd and eda may not be particularly limited as long as the microorganism belongs to the genus of *Escherichia*. For example, the microorganism producing L-tryptophan may be a microorganism in which, for enhancing the biosynthetic pathway, the activities of the gene in the competitive pathway, the regulator in the directional pathway of tryptophan operon, and the gene for introducing and decomposing tryptophan were weakened or inactivated, and/or the activity of the tryptophan operon was overexpressed. The methods of weakening or inactivating the activity are the same as explained above, and the methods known in the art are included without limitation. Additionally, the methods for overexpressing the activity of tryptophan operon known in the art are included without limitation. For example, the methods may include a method of further introducing a polynucleotide, which includes part or the entirety itself of the nucleotide sequence of the operon gene or an expression control region introduced from outside, into the chromosome; a method of increasing the copy number by introducing into a vector system; a method of enhancing operon activity by substituting the expression control sequence that controls gene expression with another expression control sequence, a modification having an induced mutation in part or the entirety of the nucleotide sequence of the expression control region, and an introduction of a modification of the gene itself, etc., but are not limited thereto. Specifically, the microorganism may be *E. coli*, in which part or the entirety of the pheA gene, trpR gene, mtr gene, and tnaAB gene are deleted and/or the tryptophan operon is overexpressed.

In the present application, edd gene, eda gene, pheA gene, trpR gene, mtr gene, tnaAB gene, and tryptophan operon, and protein sequences encoded by them may be obtained from a known database, e.g., GenBank of NCBI, but are not limited thereto. Additionally, the specific details with respect to pheA gene, trpR gene, mtr gene, and tnaAB gene may be found in the disclosure of Korean Patent No. 10-0792095, and the entire specification of this Korean Patent may be included as a reference of the present application.

From the exemplary embodiments of the present application, it was confirmed that, with respect to the inactivation of the activities of 6-phosphogluconate dehydratase and 2-keto-3-deoxy-6-phosphogluconate aldolase in various parent strains, any microorganism of the genus *Escherichia*, regardless of its parent strain, significantly improved the production of L-tryptophan when the activities of both 6-phosphogluconate dehydratase and 2-keto-3-deoxy-6-phosphogluconate aldolase were weakened or inactivated together.

In another aspect, the present application provides a method for preparing L-tryptophan, including culturing a microorganism of the genus *Escherichia* producing L-tryptophan by weakening or inactivating the activities of endogenous 6-phosphogluconate dehydratase (edd) and 2-keto-3-deoxy-6-phosphogluconate aldolase (eda) of the present application; and recovering L-tryptophan from the cultured medium or the cultured microorganism.

The medium and other culture conditions used for culturing the microorganism of the present application are not particularly limited but any medium used for the conventional cultivation of the microorganism of the genus *Escherichia* may be used. Specifically, the microorganism of the present application may be cultured in a conventional medium containing appropriate carbon sources, nitrogen sources, phosphorous sources, inorganic compounds, amino acids and/or vitamins, etc., in an aerobic condition while adjusting temperature, pH, etc.

Examples of the carbon sources to be used in the present application may include carbohydrates such as glucose, fructose, sucrose, maltose, mannitol, sorbitol, etc.; alcohols such as sugar alcohols, glycerol, pyruvate, lactate, citrate, etc.; and amino acids such as orgarnic acid, glutamic acid, methionine, lysine, etc. Additionally, natural organic nutrients such as starch hydrolysate, molasses, blackstrap molasses, rice bran, cassava starch, sugar cane molasses, corn steep liquor, etc., and specifically, carbohydrates such as glucose and sterile pretreated molasses (i.e., molasses converted to a reducing sugar), etc. Furthermore, various other carbon sources in a suitable amount may be used without limitation. These carbon sources may be used alone or in a combination of two or more.

Examples of the nitrogen sources to be used in the present application may include inorganic compounds such as ammonia, ammonium sulfate, ammonium chloride, ammonium acetate, ammonium phosphate, ammonium carbonate, ammonium nitrate, etc.; amino acids such as glutamic acid, methionine, glutamine, etc.; and organic nitrogen sources such as peptone, NZ-amine, meat extract, yeast extract, malt extract, corn steep liquor, casein hydrolysate, fish or decomposition products thereof, defatted soybean cake or decomposition products thereof, etc. These nitrogen sources may be used alone or in a combination of two or more.

Examples of the phosphorus sources to be used in the present application may include potassium phosphate monobasic, dipotassium phosphate dibasic, corresponding sodium-containing salts, etc., but are not limited thereto. Examples of inorganic compounds may include sodium chloride, calcium chloride, iron chloride, magnesium sulfate, manganese sulfate, calcium carbonate, etc., and additionally, amino acids, vitamins, and/or suitable precursors for a culture medium may be included. These medium or precursors may be added to a culture by a batch culture or continuous culture.

In the present application, the pH of a culture may be adjusted during the culture by adding a compound such as ammonium hydroxide, potassium hydroxide, ammonia, phosphoric acid, and sulfuric acid to the culture in an appropriate manner. During the culture period, an antifoaming agent, such as fatty acid polyglycol ester, may be added to prevent foam generation. Additionally, oxygen or an oxygen-containing gas may be injected into the culture in order to maintain an aerobic state of the culture; or nitrogen, hydrogen, or carbon dioxide gas may be injected without the injection of a gas in order to maintain an anaerobic or microaerobic state of the culture.

The culture temperature may generally be in a range from 27° C. to 40° C., and specifically, from 30° C. to 37° C., but is not limited thereto. The cultivation may be continued until the desired amount of useful materials are obtained, and specifically for from 10 hours to 100 hours, but is not limited thereto.

L-tryptophan may be recovered by a suitable method known in the art, e.g., batch culture, continuous culture, or fed batch culture, etc., according to the cultivation method of the present application.

The recovery may also include a step of purification.

L-amino acids may be released into the culture medium being cultured or may be contained in microorganisms.

Advantageous Effects of the Invention

The present application provides a microorganism of the genus *Escherichia* producing L-tryptophan by weakening or inactivating the activity of endogenous 6-phosphogluconate dehydratase and 2-keto-3-deoxy-6-phosphogluconate aldolase, and thus the present application provides an effect that L-tryptophan can be produced in higher yield and with higher efficiency and cost effectiveness using the microorganism.

MODES FOR CARRYING OUT THE INVENTION

Hereinbelow, the present application will be described in detail with accompanying examples. However, the examples disclosed herein are only for illustrative purposes and should not be construed as limiting the scope of the present application.

Comparative Example 1: Preparation of a Parent Strain (ΔpheAΔtrpRΔmtrΔtnaAB/pCL1920-Ptre-trpO)

(1) Preparation of a Wild-Type Strain in Which Proteins Encoded by pheA, trpR, mtr, and tnaAB Genes are Inactivated For enhancing the biosynthesis pathway of tryptophan by the parent strain, pheA gene, which is a gene in the competitive pathway; trpR gene, which is a regulator of tryptophan operon and the directional pathway; mtr gene, which is a gene for introducing tryptophan; and tnaA and tnaB genes, which are genes for introducing and decomposing tryptophan, were all inactivated, and thereby the tryptophan-producing ability of the microorganism of the present application was better examined. The chorismate mutase/prephenate hydratase encoded by pheA gene; trpR transcriptional repressor encoded by trpR gene; tryptophan/indole: symporter by mtr gene; and tryptophanase and trpytpophan: H$^+$ symporter encoded by tnaA and tnaB genes in the form of an operon were all inactivated by homologous recombination of the genes in *E. coli* W3110 (ATCC®39936™). For this purpose, the one-step inactivation method using lambda Red recombinase developed by Datsenko K A et al. was employed, and the inactivation was performed based on the method described in Korean Patent No. 10-0792095. The sequences of the primers used in Comparative Example 1 described herein, and Comparative Example 2 and Examples 1 and 3 described below are shown in Table 3 below.

Specifically, about 1,100 pairs of gene fragments were amplified by PCR using pKD3 gene as a template, along with a part of the pheA gene having a sequence of SEQ ID NO: 6 and primers 1 and 2 having a partial nucleotide sequence of the chloramphenicol-resistant gene of the pKD3 gene. Then, the DNA fragments obtained by PCR were electrophoresed in a 0.8% agarose gel, eluted, and used as a template for the second PCR. To obtain the 5' and 3' DNA fragments of the pheA gene in *E. coli*, about 250 pairs of gene fragments were amplified by PCR using the chromosome of *E. coli* W3110 as a template, along with primers 3 and 4 and primers 5 and 6. Then, the DNA fragments obtained by PCR were electrophoresed in a 0.8% agarose gel, eluted, and used as a template for the second PCR.

In the above, the nucleotide sequences of 18 pairs between primer 1 and primer 4 are complementary and the nucleotide sequences of 20 pairs between primer 2 and primer 5 are complementary, and thus the fragments obtained by primer 1 and primer 2, those obtained by primer 3 and primer 4, and those obtained by primer 5 and primer 6 can be linked as a single fragment. The thus-obtained PCR fragments were amplified 5 times by PCR without using any primer, treated with primers 3 and 6, and again amplified 25 times by PCR. As a result, gene fragments with a size of about 1,600 base pairs of were amplified.

Then, *E. coli* W3110, which was transformed with pKD46, was prepared into competent cells according to the method developed by Datsenko K A et al., introduced with gene fragments with a size of about 1,600 base pairs obtained by PCR, and plated on LB solid medium containing chloramphenicol (30 mg/L). After confirming by PCR that the pheA gene in the thus-obtained strain was inactivated by having a size of 1,600 base pairs, the *E. coli* W3110 zipheA strain was prepared.

Likewise the proteins encoded by the trpR gene having the sequence of SEQ ID NO: 8, the mtr gene having the sequence of SEQ ID NO: 10, and by the tnaA and tnaB genes having the sequences of SEQ ID NOS: 12 and 14 were inactivated using the primers in Table 3, thereby constructing a W3110 ΔpheAΔtrpRAmtrΔtnaAB strain.

(2) Preparation of Vectors Introduced with Genes Exhibiting the Ability to Produce Tryptophan In order to provide an ability to produce tryptophan to the wild-type strain, W3110ΔpheAΔtrpRΔmtrΔtnaAB, prepared above, the pCL1920 vector was inserted with Ptrc promoter and tryptophan operon gene and thereby pCL1920-Ptrc-trpO was prepared.

Specifically, for inserting the Ptrc promoter into the pCL1920 vector, the pCL1920 plasmid was recovered, treated with HindIII and PstI, and the Ptrc promoter was prepared by PCR by repeating 30 cycles of denaturation at 94° C. for 30 seconds, annealing at 58° C. for 30 seconds, and polymerization at 72° C. for 30 seconds using pTrcHis B (Invitrogen, USA) as a template along with primers 23 and 24. The thus-obtained Ptrc promoter fragments were cleaved with HindIII and PstI, and ligated with the pCL1920 vector, thereby constructing a pCL1920 Ptrc vector.

Then, for constructing the pCL1920_Ptrc_trpO vector, the pCL1920-Ptrc vector was prepared by treating with PstI and alkaline phosphatase, and the tryptophan operon gene was amplified from the chromosomal DNA of *E. coli* KCCM10812P (Korean Patent No. 10-0792095). The trpE gene, which is the first gene of the corresponding operon gene, has a feedback inhibition form. For the amplification, PCR was performed using the chromosomal DNA of *E. coli* KCCM10812P as a template along with primers 25 and 26 by repeating 30 cycles of denaturation at 94° C. for 30 seconds, annealing at 58° C. for 30 seconds, and polymerization at 72° C. for 5 minutes. The thus-obtained DNA fragments were treated with PstI and ligated with the pCL1920-Ptrc vector prepared in advance, and the vector obtained as a result was named as pCL1920_Ptrc_trpO (SEQ ID NO: 15).

(3) Preparation of a Strain Inserted with a Vector Containing Tryptophan Operon

After preparing the strain prepared in Comparative Example 1 (1) into competent cells, the strain was introduced with the vector prepared in Comparative Example 1 (2), and thereby a wild-type strain W3110 ΔpheAΔtrpRΔmtrΔtnaAB/pCL1920-Ptrc-trpO producing tryptophan was prepared.

Example 1: Preparation of a ΔeddΔeda Strain from the Parent Strain of Comparative Example 1

In the wild-type strain W3110 ΔpheAΔtrpRΔmtrΔtnaAB/ pCL1920-Ptrc-trpO prepared in Comparative Example 1, the edd-eda gene group was deleted simultaneously by homologous recombination, and thereby a strain, in which both 6-phosphogluconate dehydratase and 2-keto-3-deoxy-6-phosphogluconate, encoded by the edd gene (SEQ ID NO: 2) and the eda gene (SEQ ID NO: 4), were both inactivated, was prepared.

Specifically, for the preparation of the above strain, the one-step inactivation method, which is a mutant-generating technology using lambda Red recombinase developed by Datsenko K A et al., was used. As the marker for confirming the insertion into a gene, chloramphenicol gene of pUCprmfmloxC was used (Korean Patent Application Publication No. 2009-007554). About 1,200 pairs of gene fragments were amplified by PCR by repeating 30 cycles of denaturation at 94° C. for 30 seconds, annealing at 55° C. for 30 seconds, and polymerization at 72° C. for 1 minute, using pUCprmfmloxC as a template along with primers 27 and 28 having a part of the edd-eda gene group and a partial nucleotide sequence of the chloramphenicol-resistant gene of the pUCprmfmloxC gene.

Additionally, the DNA fragments obtained by PCR amplification were electrophoresed in a 0.8% agarose gel, eluted, and used as a template for the second PCR. The second PCR was designed to obtain 20 pairs of complementary nucleotide sequences in the 5' and 3' regions of the first DNA fragments, and about 1,300 pairs of gene fragments were amplified by PCR by repeating 30 cycles of denaturation at 94° C. for 30 seconds, annealing at 55° C. for 30 seconds, and polymerization at 72° C. for 1 minute, using the first PCR product as a template along with primers 29 and 30, to which the 5' and 3' regions of the edd-eda gene group were added. The thus-obtained DNA fragments were electrophoresed in a 0.8% agarose gel, eluted, and used for recombination.

The *E. coli* transformed with pKD46 according to the method developed by Datsenko K A et al. was prepared in a competent state, and the gene fragment with a size of 1,300 base pairs obtained by PCR was introduced therein for transformation. The thus-obtained strain was selected in LB medium containing chloramphenicol, and the PCR product obtained using primers 31 and 32 had a size of 1,626 base pairs, thus confirming that the edd-eda gene group was deleted.

The first recombinant strain having chloramphenicol resistance, after removing pKD46, was introduced with pJW 168, thereby removing chloramphenicol marker gene from the bacterial body (Gene, (2000) 247, 255-64). The finally-obtained bacterial body was a PCR-amplified product, obtained using primers 31 and 32, having a size of 580 pairs, thus confirming that the intended deletion was made. Additionally, after preparing the strain in a competent state, the strain was transformed by introducing the vector prepared in Comparative Example 1 therein, thereby preparing a W3110ΔpheAΔtrpRΔmtrΔtnaABΔeddΔeda/pCL1920-Ptrc-trpO strain producing tryptophan.

Example 2: Confirmation of the Tryptophan-Producing Ability of ΔeddΔeda Strain

Titer evaluation was performed using the strain prepared in Comparative Example 1 and Example 1. For the titer evaluation, the bacterial body was inoculated with a platinum loop, cultured in solid LB medium overnight, and inoculated with a platinum loop onto each 25 mL flask titer medium having the composition shown in Table 1 below. After the inoculation, the strain was cultured at 37° C. at a rate of 200 rpm for 42 hours, and the results obtained therefrom are shown in Table 2 below. All results used represent the average value of the results obtained from three different flasks.

TABLE 1

| Composition | Concentration (per liter) |
|---|---|
| Glucose | 30 g |
| $K_2HPO_4$ | 1 g |
| $(NH_4)_2SO_4$ | 10 g |
| NaCl | 1 g |
| $MgSO_4 \cdot 7H_2O$ | 1 g |
| Sodium citrate | 5 g |
| Yeast extract | 2 g |
| Calcium carbonate | 40 g |
| Sodium citrate | 5 g |
| Phenylalanine | 0.15 g |
| Tyrosine | 0.1 g |
| pH | 6.8 g |

TABLE 2

| Strain | OD | Glucose Consumption (g/L)* | L-tryptophan (g/L)** |
|---|---|---|---|
| W3110ΔpheAΔtrpRΔmtrΔtnaAB/pCL1920-Ptrc-trpO | 30.1 | 24.7 | 0.78 |
| Example 1 (W3110ΔpheAΔtrpRΔmtrΔtnaABΔeddΔeda/pCL1920-Ptrc-trpO) | 29.5 | 25.1 | 1.03 |

*value measured at the time-point of 22 hours
**value measured at the time-point of 42 hours As a result of the above experiment, as shown in Table 2 above, when the edd-eda gene group suggested in the present application was deleted, there was no significant difference in the glucose consumption compared to that of the parent strain in Comparative Example 1, however, the amount of tryptophan production was shown to increase by about 32% compared to that of the parent strain. This result is thought to be due to the fact that the reaction proceeded to ribulose 5-phosphate without the loss of 6-phosphogluconate, which is a substrate, by the deletion in the Entner Doudoroff pathway, and thus not only the amount of NADPH but also the amount of 5-phosphoribosyl-1-pyrophosphate (PRPP) and erythrose 4-phosphate (E4P) was increased, thereby improving the ability to produce tryptophan.

Example 3: Preparation of a ΔeddΔeda Strain from the Deposited Parent Strain

The L-tryptophan-producing *E. coli* KCCM11166P (Korean Patent No. 10-1261147) deposited in the Korean Culture Center of Microorganisms (KCCM) was treated in the same manner as in Example 1 and thereby a KCCM11166PΔeddΔeda strain, in which the edd-eda gene group was deleted, was prepared.

TABLE 3

| Gene | Primer No. | Sequence (5'→3') | SEQ ID NO |
|---|---|---|---|
| pheA | 1 | AGGCAACACTATGACATCGTGTAGGCTGGAGCTGCTTC | 16 |
| | 2 | GGTCGCCATTAACAACGTGGCATATGAATATCCTCCTTAG | 17 |
| | 3 | TATTGAGTGTATCGCCAAC | 18 |
| | 4 | CGATGTCATAGTGTTGCC | 19 |
| | 5 | CCACGTTGTTAATGGCGACC | 20 |
| | 6 | TTCATTGAACGGGTGATTTC | 21 |
| trpR | 7 | TCCGCACGTTTATGATATGCTATCGTACTCTTTAGCGAGTACAACCGGGGTGTAGGCTGGAGCTGCTTC | 22 |
| | 8 | GCCACGTCTTATCAGGCCTACAAAATCAATCGCTTTTCAGCAACACCTCTCATATGAATATCCTCCTTAG | 23 |
| | 9 | GCGCCGGGCGTATCGACGCA | 24 |
| | 10 | GCATATCATAAACGTGCGGA | 25 |
| | 11 | TGTAGGCCTGATAAGACGTG | 26 |
| | 12 | AAGGGGCGATCGGCGTGTTT | 27 |
| mtr | 13 | ATGGCAACACTAACCACCACCCAAACGTCACCGTCGCTGCTTGGCGGCGTGTGTAGGCTGGAGCTGCTTC | 28 |
| | 14 | TTACTGATACACCGGCAGTAAATTAAAGCTCGATAAAATATGCACCAGTGCATATGAATATCCTCCTTAG | 29 |
| | 15 | GCAGCCGTTACATTGGTAAC | 30 |
| | 16 | GTGGTGGTTAGTGTTGCCAT | 31 |
| | 17 | TACTGCCGGTGTATCAGTAA | 32 |
| | 18 | TCAAACCGTCAGCACGGCTG | 33 |
| tnaAB | 19 | ATGAAGGATTATGTAATGGAAAACTTTAAACATCTCCCTGAACCGTTCCGGTGTAGGCTGGAGCTGCTTC | 34 |
| | 20 | TTAGCCAAATTTAGGTAACACGTTAAAGACGTTGCCGAACCAGCACAAAACATATGAATATCCTCCTTAG | 35 |
| | 21 | TTAAGCGAAATCACCGGGGAA | 36 |
| | 22 | ATGTCCGAGCACTGGCGC | 37 |
| pCL1920-Ptrc-trpO | 23 | CCCAAGCTTGCTGTTGACAATTAATCAT | 38 |
| | 24 | AAAACTGCAGCTGTTTCCTGTGTGAAAT | 39 |
| | 25 | AAAACTGCAGATGCAAACACAAAAACCGACT | 40 |
| | 26 | AAAACTGCAGTTAACTGCGCGTCGCCGCTTTC | 41 |
| edd-eda | 27 | AAACGCGTTGTGAATCATCCTGCTCTGACAACTCAATTTCAGGAGCCTTTGCCGCCAGCTGAAGCTTTAC | 42 |
| | 28 | ACAGCACGCTTTTCAGCGCCAGGTAGTCACGGTAGTTAGCCGGAGAAATATAGTGGATCTGATGGGTACC | 43 |
| | 29 | TGCCCTATGAGCTCCGGTTACAGGCGTTTCAGTCATAAATCCTCTGAATGAAACGCGTTGTGAATCATCC | 44 |
| | 30 | ATCGCCCGCTTCCAGCGCATCTGCCGGAACCAGCCAGGAACCACCGATGCACAGCACGCTTTTCAGCGCC | 45 |
| | 31 | CATGATCTTGCGCAGATTGTA | 46 |
| | 32 | CATGATCTTGCGCAGATTGTA | 47 |

Example 4: Confirmation of the Tryptophan-Producing Ability of ΔeddΔeda Strain

Titer evaluation was performed using the deposited strain KCCM11166P and the strain prepared in Example 3.

For the titer evaluation, the bacterial body was inoculated with a platinum loop, cultured in solid LB medium overnight, and inoculated with a platinum loop onto each 25 mL flask titer medium having the composition shown in Table 4 below. After the inoculation, the strain was cultured at 37° C. at a rate of 200 rpm for 42 hours, and the results obtained therefrom are shown in Table 5 below. All results used represent the average value of the results obtained from three different flasks.

TABLE 4

| Composition | Concentration (per liter) |
|---|---|
| Glucose | 60 g |
| $K_2HPO_4$ | 1 g |
| $(NH_4)_2SO_4$ | 10 g |
| NaCl | 1 g |
| $MgSO_4 \cdot 7H_2O$ | 1 g |
| Sodium citrate | 5 g |
| Yeast extract | 2 g |
| Calcium carbonate | 40 g |
| Sodium citrate | 5 g |
| Phenylalanine | 0.15 g |
| Tyrosine | 0.1 g |
| pH | 6.8 g |

TABLE 5

| Strain | OD | Glucose Consumption (g/L)* | L-tryptophan (g/L)** |
| --- | --- | --- | --- |
| KCCM11166P | 22.9 | 31.0 | 5.7 |
| KCCM11166PΔeddΔeda | 23.6 | 30.7 | 6.9 |

*value measured at the time-point of 33 hours
**value measured at the time-point of 48 hours As a result of the above experiment, as shown in Table 5 above, when the edd-eda gene group suggested in the present application was deleted, there was no significant difference in the glucose consumption compared to that of the parent strain, however, the amount of tryptophan production was shown to increase by about 21% compared to that of the parent strain. This result is thought to be due to the improvement in the tryptophan-producing ability, as mentioned in Example 2 above.

The present inventors have confirmed that the KCCM11166P-based strain, in which the edd-eda gene group was inactivated, has an improved tryptophan-producing ability, named the strain as "CA04-2800", and deposited it to the KCCM on Nov. 15, 2013, and it was assigned the deposit number KCCM11473P.

The above results suggest that the simultaneous inactivation of edd-eda activities in a microorganism of the genus Escherichia having the Entner-Doudoroff pathway can improve the tryptophan-producing ability, compared to the microorganism without the inactivation of edd-eda activities.

In the present application, the detailed description of those which can be sufficiently acknowledged and drawn by one of ordinary skill in the art is omitted, and various modifications, in addition to the exemplary embodiments described herein, may be included within the spirit and scope of the present application without modifying the technical concepts or essential characteristics of the present application. Accordingly, the present application may be embodied in other specific forms and one of ordinary skill in the art to which the present application pertains will be able to understand the same.

[Deposit Number]
Deposit Authority: Korean Culture Center of Microorganisms (overseas)
Deposit Number: KCCM11473P
Date of Deposit: 20131115

The invention claimed is:

1. A microorganism of the genus *Escherichia* producing L-tryptophan, wherein the activities of endogenous 6-phosphogluconate dehydratase (Edd) and 2-keto-3-deoxy-6-phosphogluconate aldolase (Eda) are weakened or inactivated, wherein the microorganism has a weakened or blocked Entner-Doudoroff pathway thereby does not lose 6-phosphogluconate, and wherein an entirety or a part of the pheA gene, trpR gene, mtr gene, and tnaAB gene is further deleted.

2. The microorganism according to claim 1, wherein the 6-phosphogluconate dehydratase has the amino acid sequence set forth in SEQ ID NO: 1.

3. A method of preparing L-tryptophan, comprising: culturing the microorganism of the genus *Escherichia* of claim 2 in a medium; and recovering L-tryptophan from the cultured medium or the cultured microorganism.

4. The microorganism according to claim 1, wherein the 2-keto-3-deoxy-6-phosphogluconate aldolase has the amino acid sequence set forth in SEQ ID NO: 3.

5. A method of preparing L-tryptophan, comprising: culturing the microorganism of the genus *Escherichia* of claim 4 in a medium; and recovering L-tryptophan from the cultured medium or the cultured microorganism.

6. The microorganism according to claim 1, wherein the microorganism of the genus *Escherichia* is *Escherichia coli*.

7. A method of preparing L-tryptophan, comprising: culturing the microorganism of the genus *Escherichia* of claim 6 in a medium; and recovering L-tryptophan from the cultured medium or the cultured microorganism.

8. A method of preparing L-tryptophan, comprising: culturing the microorganism of the genus *Escherichia* of claim 1 in a medium; and recovering L-tryptophan from the cultured medium or the cultured microorganism.

9. A method of preparing L-tryptophan, comprising: culturing a microorganism of the genus *Escherichia* producing L-tryptophan, wherein the activities of endogenous 6-phosphogluconate dehydratase (Edd) and 2-keto-3-deoxy-6-phosphogluconate aldolase (Eda) are weakened or inactivated, wherein the microorganism has a blocked Entner-Doudoroff pathway thereby does not lose 6-phosphogluconate in a medium, and wherein the microorganism has higher L-tryptophan production relative to an identical microorganism with the proviso the Edd and Eda are not weakened or inactivated; and recovering L-tryptophan from the cultured medium or the cultured microorganism.

10. The method according to claim 9, wherein the microorganism of the genus *Escherichia* is *Escherichia coli*.

* * * * *